United States Patent
Sakaguchi et al.

(10) Patent No.: US 9,072,490 B2
(45) Date of Patent: Jul. 7, 2015

(54) IMAGE PROCESSING APPARATUS AND IMAGE PROCESSING METHOD

(75) Inventors: Takuya Sakaguchi, Shioya-gun (JP); Hisato Takemoto, Nasushiobara (JP); Joao A. C. Lima, Baltimore, MD (US); Richard T. George, Baltimore, MD (US); Jeff Trost, Baltimore, MD (US)

(73) Assignees: Toshiba Medical Systems Corporation, Otawara-shi (JP); The Johns Hopkins University, Baltimore, MD (US)

( * ) Notice: Subject to any disclaimer, the term of this patent is extended or adjusted under 35 U.S.C. 154(b) by 1030 days.

(21) Appl. No.: 12/973,115

(22) Filed: Dec. 20, 2010

(65) Prior Publication Data
US 2012/0155737 A1  Jun. 21, 2012

(51) Int. Cl.
G06K 9/00 (2006.01)
A61B 6/00 (2006.01)
(Continued)

(52) U.S. Cl.
CPC ............... *A61B 6/463* (2013.01); *A61B 5/055* (2013.01); *A61B 6/503* (2013.01); *A61B 6/504* (2013.01); *G06T 5/50* (2013.01); *G06T 2207/10116* (2013.01); *G06T 2207/20224* (2013.01);
(Continued)

(58) Field of Classification Search
USPC ......... 382/100, 107, 128–134, 153, 168, 181, 382/190–197, 199, 203, 209, 232, 236, 256, 382/275–276, 280, 283–284, 285–297, 305, 382/312; 128/920, 922; 345/419, 422; 348/207.99, 699; 378/95, 196, 62, 4, 8, 378/98.11–98.12, 98, 21, 27; 424/486; 600/410, 431, 425, 407, 481
See application file for complete search history.

(56) References Cited

U.S. PATENT DOCUMENTS

| | | | | |
|---|---|---|---|---|
| 5,150,292 | A | * | 9/1992 | Hoffmann et al. ............ 600/431 |
| 5,848,121 | A | * | 12/1998 | Gupta et al. .................... 378/62 |
| 6,154,518 | A | * | 11/2000 | Gupta ............................. 378/62 |

(Continued)

FOREIGN PATENT DOCUMENTS

| | | |
|---|---|---|
| CN | 101803931 A | 8/2010 |
| JP | 2005-124617 | 5/2005 |

(Continued)

OTHER PUBLICATIONS

Office Action issued Oct. 10, 2014, in Chinese Patent Application No. 201110133340.8.

(Continued)

*Primary Examiner* — Hadi Akhavannik
(74) *Attorney, Agent, or Firm* — Oblon, McClelland, Maier & Neustadt, L.L.P.

(57) ABSTRACT

In one embodiment, an image processing apparatus includes a difference image generating unit and a display controlling unit. The difference image generating unit generates a difference image by calculating a difference in a second X-ray transmission image from a first X-ray transmission image, the second X-ray transmission image being an image in which a myocardial tissue of an examined subject is not opacified and the first X-ray transmission image being an image in which the myocardial tissue of the examined subject is opacified with a contrast agent that has been injected into a coronary artery. The display controlling unit exercises control so that a predetermined display unit displays the difference image that has been generated by the difference image generating unit.

20 Claims, 18 Drawing Sheets

(51) Int. Cl.
*A61B 5/055* (2006.01)
*G06T 5/50* (2006.01)

(52) U.S. Cl.
CPC ............... *G06T2207/30048* (2013.01); *G06T 2207/30101* (2013.01); *A61B 6/507* (2013.01)

(56) References Cited

U.S. PATENT DOCUMENTS

| | | | |
|---|---|---|---|
| 7,496,175 B2 | 2/2009 | Sakaguchi et al. | |
| 7,545,967 B1* | 6/2009 | Prince et al. | 382/130 |
| 7,697,740 B2* | 4/2010 | Fujisawa | 382/128 |
| 7,907,217 B2* | 3/2011 | Baumgart et al. | 348/699 |
| 8,090,176 B2* | 1/2012 | Kinnstaetter et al. | 382/130 |
| 2001/0002993 A1* | 6/2001 | Ostensen et al. | 424/9.52 |
| 2005/0277830 A1* | 12/2005 | Ichihara | 600/425 |
| 2006/0093198 A1* | 5/2006 | Fram et al. | 382/128 |
| 2007/0036269 A1* | 2/2007 | Lienard et al. | 378/98.12 |
| 2007/0092067 A1* | 4/2007 | Fujisawa | 378/196 |
| 2007/0127789 A1* | 6/2007 | Hoppel et al. | 382/128 |
| 2007/0154555 A1* | 7/2007 | Strauss et al. | 424/486 |
| 2008/0101670 A1* | 5/2008 | Baumgart et al. | 382/128 |
| 2008/0107233 A1* | 5/2008 | Sakaguchi et al. | 378/91 |
| 2008/0267861 A1* | 10/2008 | Lieu et al. | 424/1.11 |
| 2008/0317323 A1* | 12/2008 | Kinnstaetter et al. | 382/132 |
| 2009/0005672 A1* | 1/2009 | Sugiura | 600/419 |
| 2009/0110252 A1* | 4/2009 | Baumgart et al. | 382/130 |
| 2009/0306500 A1* | 12/2009 | Rahn et al. | 600/431 |
| 2010/0128991 A1* | 5/2010 | Weese et al. | 382/209 |
| 2010/0172474 A1* | 7/2010 | Vogt et al. | 378/98.12 |
| 2011/0037761 A1* | 2/2011 | Mistretta et al. | 345/419 |
| 2011/0038517 A1* | 2/2011 | Mistretta et al. | 382/128 |
| 2013/0094734 A1* | 4/2013 | Rauch et al. | 382/130 |

FOREIGN PATENT DOCUMENTS

| | | |
|---|---|---|
| JP | 2010-522598 | 7/2010 |
| JP | 2010-240156 | 10/2010 |

OTHER PUBLICATIONS

Office Action Mailed Jan. 13, 2015, in Japanese Patent Application No. 2011-091438 (with English Translation).

* cited by examiner

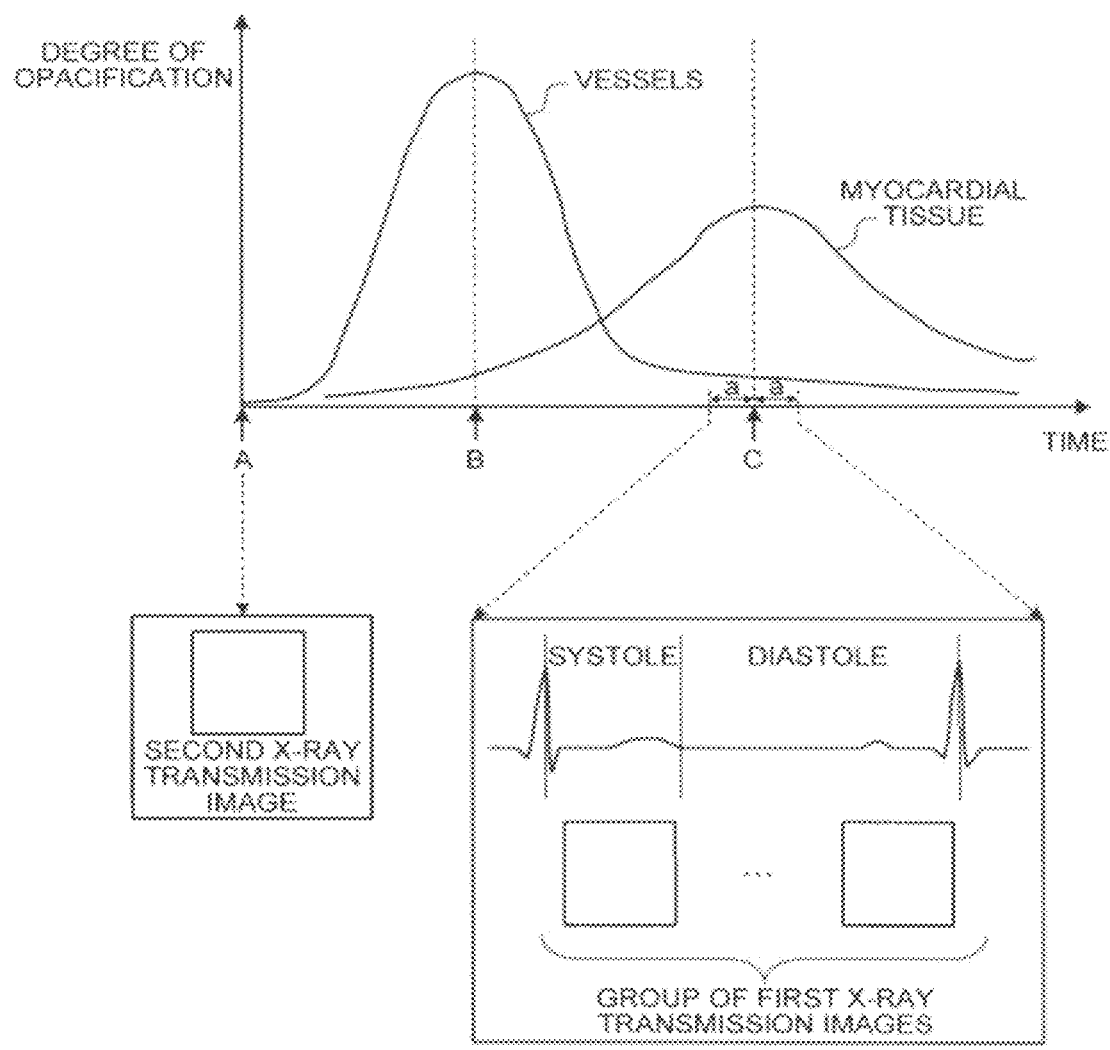

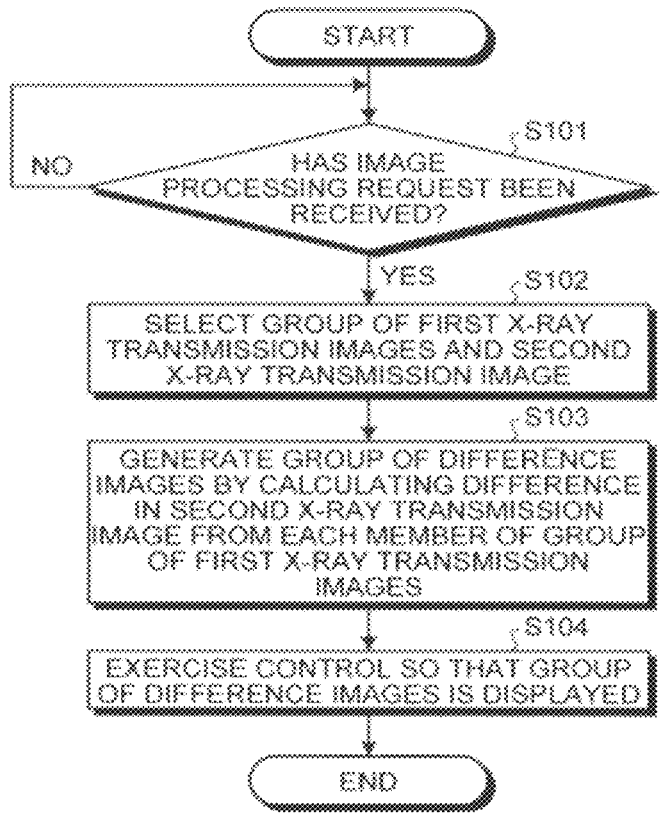
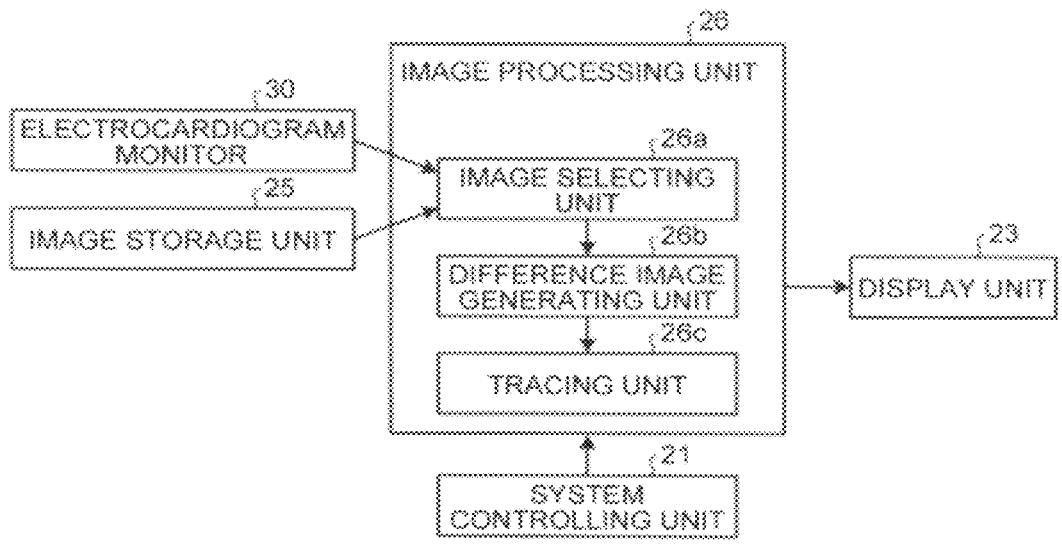

FIG.8A
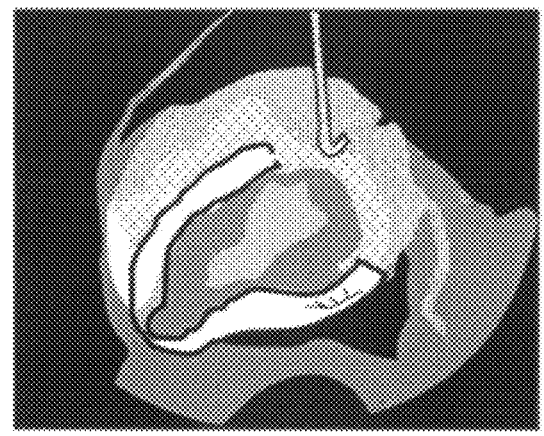
FIG.8B
DIFFERENCE IMAGE
(MYOCARDIAL TISSUE)
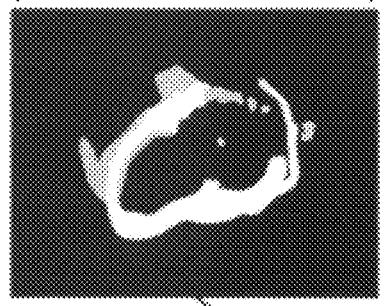
IMAGE IN WHICH VESSELS
ARE EASILY OBSERVED
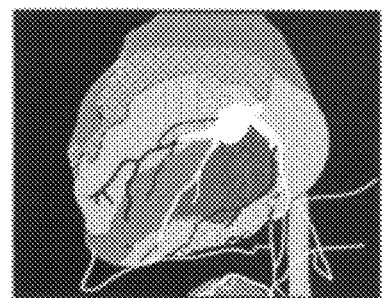
COMBINED IMAGE
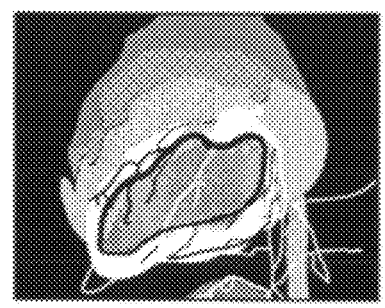

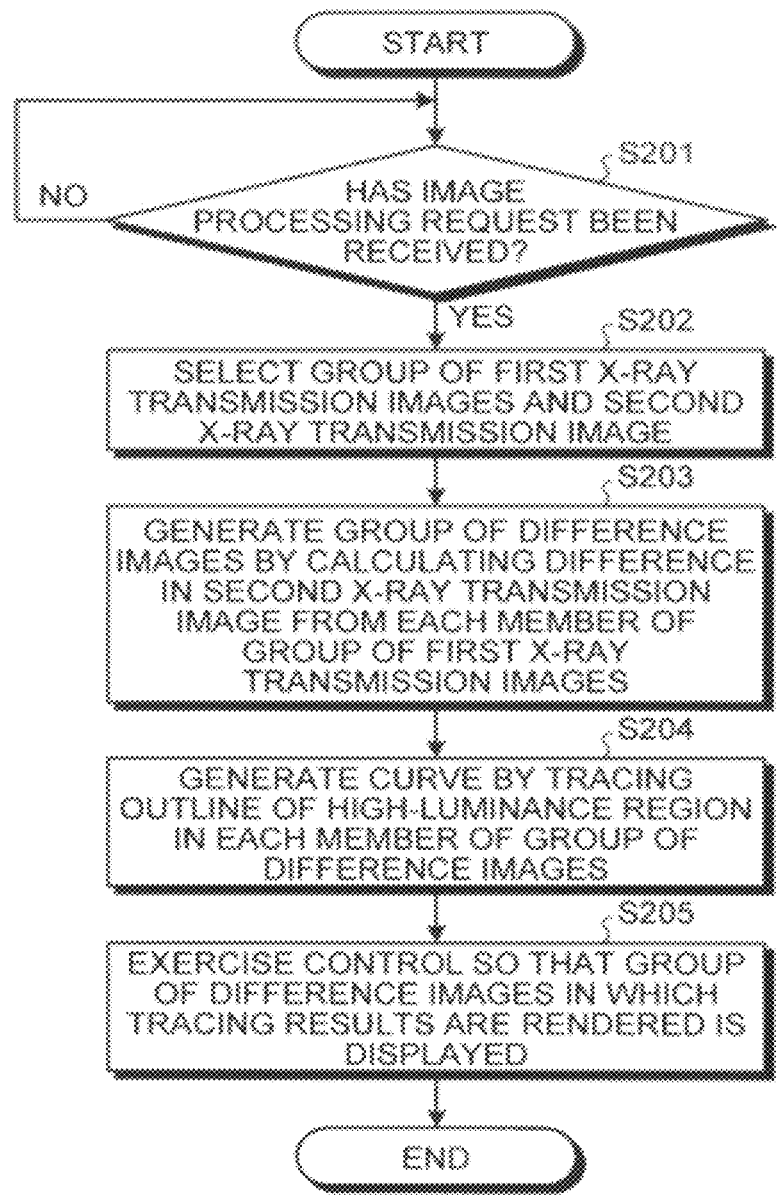

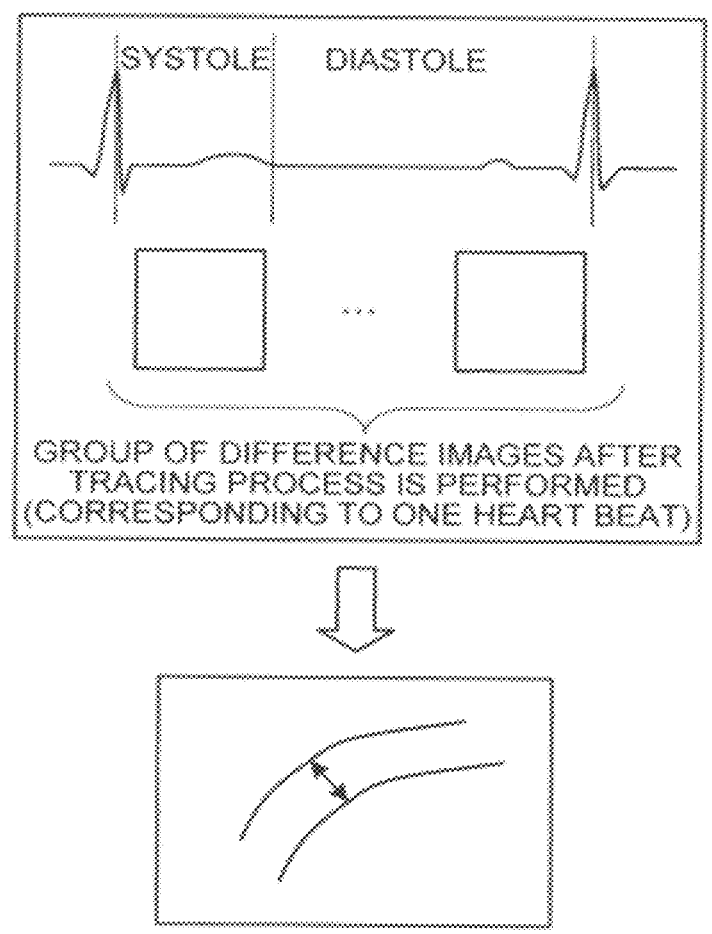

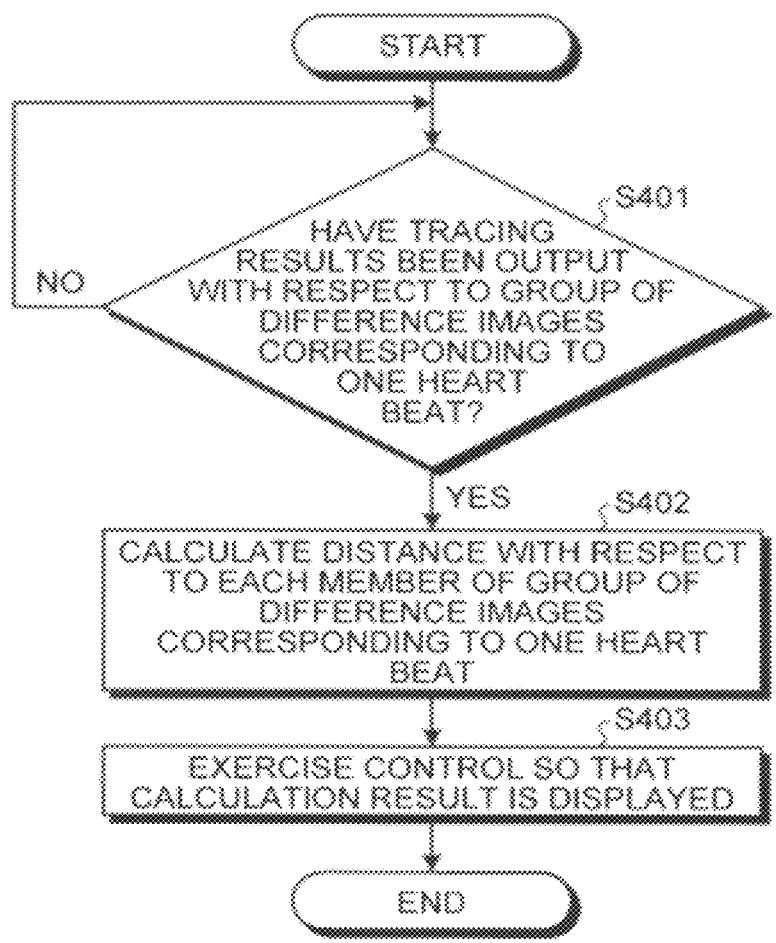

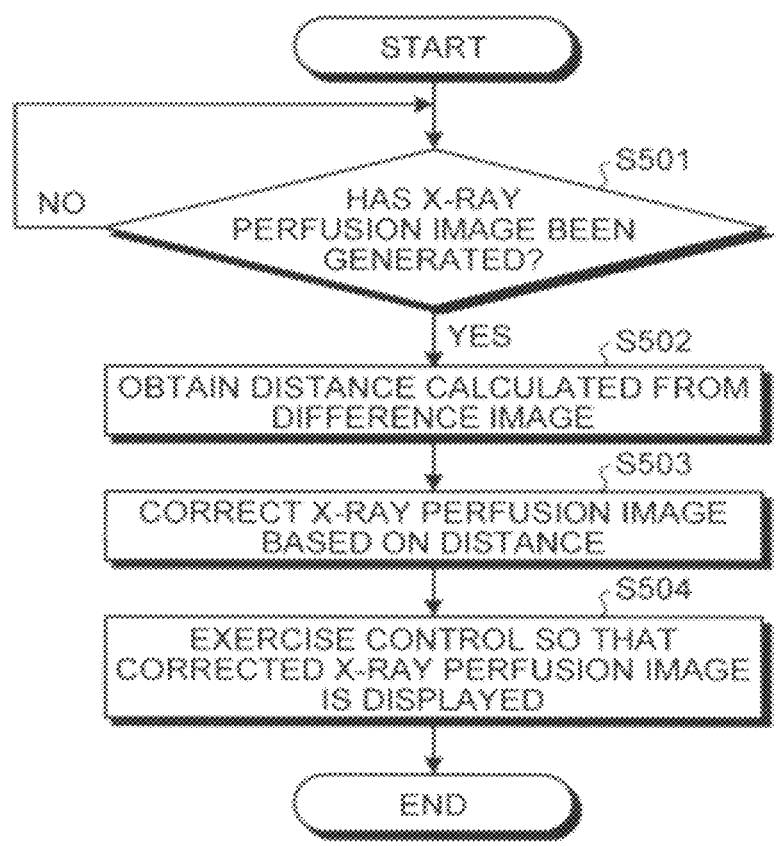

IMAGE PROCESSING APPARATUS AND IMAGE PROCESSING METHOD

FIELD

Embodiments described herein relate generally to an image processing apparatus and an image processing method.

BACKGROUND

To examine cardiac functions in the field of cardiovascular internal medicine, image diagnosis processes have conventionally been performed by using medical images that have been taken by employing medical image diagnostic apparatuses such as X-ray diagnostic apparatuses, X-ray Computed Tomography (CT) apparatuses, Magnetic Resonance Imaging (MRI) apparatuses, nuclear medicine diagnostic apparatuses, and ultrasonic diagnostic apparatuses.

As an example of a method for supporting such image diagnosis processes to examine cardiac functions, a method is known by which a plurality of points are set in the heart included in volume data that has been collected by a medical image diagnostic apparatus while using a predetermined time interval so that an image in which movement functions of the heart are rendered is displayed by tracking the plurality of points that have been set. As another example of image diagnosis process supporting methods, another method is known by which movement functions of the heart are analyzed by extracting images of an inner membrane and an outer membrane of the myocardia, out of an MRI image taken by using an image taking method that causes the luminance value of the myocardia to be higher than the luminance value of the lumen of the heart and another MRI image taken by using an image taking method employing a contrast agent that causes the luminance value of the lumen of the heart to be higher than the luminance value of the myocardia.

To examine cardiac functions by using X-ray transmission images that have been taken by X-ray diagnostic apparatuses, Left Ventriculography (LVG) processes are commonly performed. An LVG process is performed so as to take an X-ray transmission image in which the myocardium of the left ventricle is opacified by injecting a contrast agent through an LVG-purpose pig tail catheter inserted into the left ventricle of the heart. When X-ray transmission images have sequentially been taken by performing such an LVG process, medical doctors are able to make a diagnosis regarding, for example, degradation of the movement functions of the heart by referring to the images rendering the manner in which the myocardial tissue moves. Further, by calculating an Ejection Fraction (EF) value of the left ventricle, based on an X-ray transmission image that has been taken by performing an LVG process, medical doctors are able to quantitatively analyze movement functions of the heart.

Generally speaking, to examine cardiac functions by using X-ray diagnostic apparatuses, a diagnosis regarding vessel stenosis or the like is made first by taking an X-ray transmission image through a coronary angiography process, before a further diagnosis is made by performing an LVG process.

To perform the LVG process described above, for example, 30 milliliters of contrast agent is injected for performing one LVG image taking process, because it is necessary to take an image of the inside of the left ventricle without missing any part thereof. In contrast, the amount of contrast agent that is required to perform a coronary angiography process is 6 milliliters to 15 milliliters. As understood from the above, a large amount of contrast agent needs to be injected to perform an LVG process. In addition, to avoid laying a burden on the functions of the kidney, an upper limit is set for the amount of contrast agent that can be injected into an examined subject during one examination process. Thus, it is difficult to repeatedly perform the LVG process a plurality of times, because a large amount of contrast agent needs to be injected.

Further, the image-taking time period required to perform a coronary angiography process is about 5 seconds. In contrast, the image-taking time period required to perform an LVG process is longer (e.g., about 10 seconds to 20 seconds). Thus, the X-ray exposure amount during an LVG process is larger. In addition, an LVG process requires the use of a dedicated catheter as explained above. For this reason, in the case where an LVG process is performed after a coronary angiography process is performed, it is necessary to insert an LVG-purpose catheter into an examined subject after a coronary-angiography-purpose catheter has been removed. Thus, it takes a longer period of time to perform the examination.

As explained above, analyzing movement functions of the heart by using X-ray transmission images that have been taken through an LVG process has a problem where a burden is laid on the examined subject.

BRIEF DESCRIPTION OF THE DRAWINGS

FIGS. 4A, 4B and 4C are drawings for explaining the image selecting unit;

FIG. 6 is a flowchart for explaining a process performed by the X-ray diagnostic apparatus according to the first embodiment;

FIG. 7 is a drawing for explaining a configuration of an X-ray diagnostic apparatus according to a second embodiment;

FIGS. 8A and 8B are drawings for explaining a tracing unit;

FIG. 9 is a flowchart for explaining a process performed by the X-ray diagnostic apparatus according to the second embodiment;

FIGS. 15, 16A, 16B, and 16C are drawings for explaining the distance calculator;

FIG. 17 is a flowchart for explaining a process performed by the X-ray diagnostic apparatus according to the fourth embodiment;

FIG. 21 is a flowchart for explaining a process performed by the X-ray diagnostic apparatus according to the fifth embodiment.

DETAILED DESCRIPTION

In one embodiment, an image processing apparatus includes a difference image generating unit and a display controlling unit. The difference image generating unit generates a difference image by calculating a difference in a second X-ray transmission image from a first X-ray transmission image, the second X-ray transmission image being an image in which a myocardial tissue of an examined subject is not opacified and the first X-ray transmission image being an image in which the myocardial tissue of the examined subject is opacified with a contrast agent that has been injected into a coronary artery. The display controlling unit exercises control so that a predetermined display unit displays the difference image that has been generated by the difference image generating unit.

In the following sections, exemplary embodiments of an image processing apparatus and an image processing method will be explained in detail, with reference to the accompanying drawings. As the exemplary embodiments below, examples in each of which an image processing apparatus that implements an image processing method is incorporated into an X-ray diagnostic apparatus will be explained.

Figure 1:
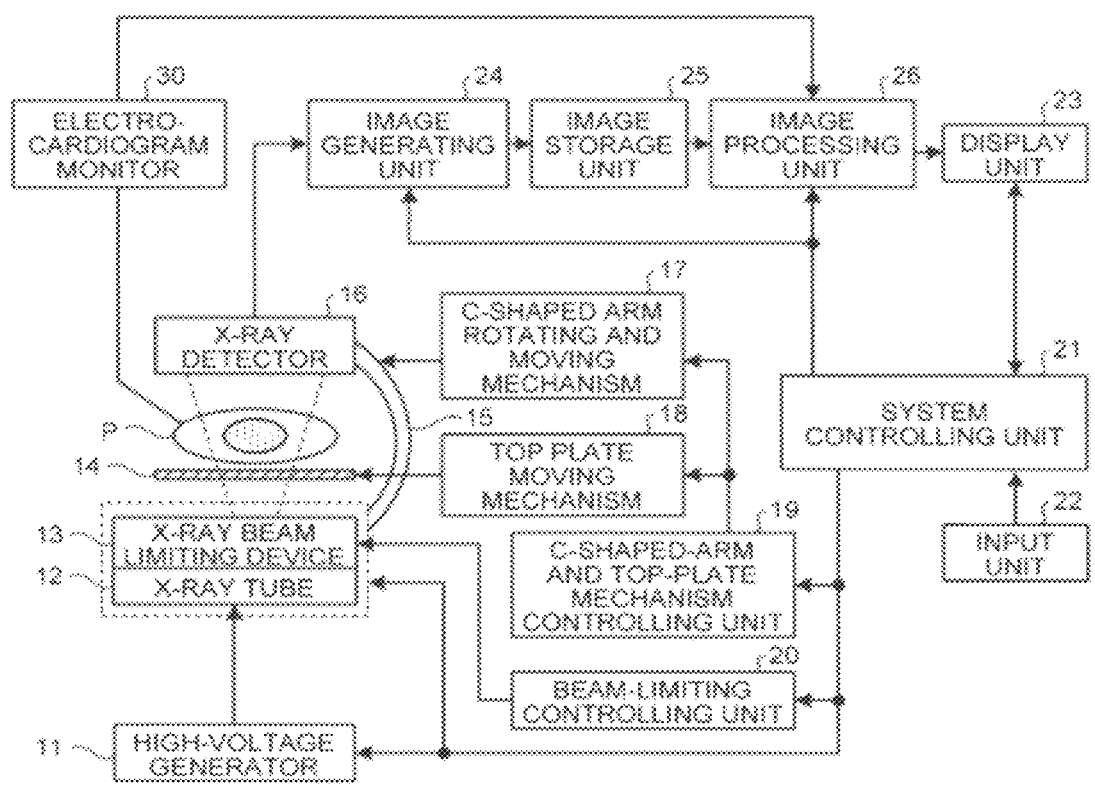
FIG. 1 is a drawing for explaining a configuration of an X-ray diagnostic apparatus according to a first embodiment.

First, a configuration of an X-ray diagnostic apparatus according to a first embodiment of the present invention will be explained. FIG. 1 is a drawing for explaining a configuration of the X-ray diagnostic apparatus according to the first embodiment.

As shown in FIG. 1, the X-ray diagnostic apparatus according to the first embodiment includes a high-voltage generator 11, an X-ray tube 12, an X-ray beam limiting device 13, a top plate 14, a C-shaped arm 15, an X-ray detector 16, a C-shaped arm rotating and moving mechanism 17, a top plate moving mechanism 18, a C-shaped-arm and top-plate mechanism controlling unit 19, a beam-limiting controlling unit 20, a system controlling unit 21, an input unit 22, a display unit 23, an image generating unit 24, an image storage unit 25, and an image processing unit 26. Further, as shown in FIG. 1, the X-ray diagnostic apparatus according to the first embodiment is configured so that an electrocardiogram monitor 30 attached to an examined subject (hereinafter, "the subject") P is connected to the image processing unit 26.

The electrocardiogram monitor 30 obtains an electrocardiogram waveform of the subject P and transmits the obtained electrocardiogram waveform to the image processing unit 26 (explained later), together with time information.

The high-voltage generator 11 is a device that generates a high voltage and supplies the generated high voltage to the X-ray tube 12. The X-ray tube 12 generates an X-ray by using the high voltage supplied from the high-voltage generator 11.

The X-ray beam limiting device 13 is a device for limiting X-ray beams generated by the X-ray tube 12 so that the X-ray beams are selectively radiated onto a region of interest of the subject P. For example, the X-ray beam limiting device 13 includes four beam-limiting blades that are slidable and slides these beam-limiting blades. With this arrangement, the X-ray beams generated by the X-ray tube 12 can selectively be radiated onto, for example, a region of interest of the subject P including the heart.

The top plate 14 is a bed on which the subject P is placed and is provided on a bed table (not shown).

The X-ray detector 16 is a device in which a plurality of X-ray detecting elements used for detecting X-ray beams that have passed through the subject P are arranged. The X-ray detecting elements convert the X-ray beams that have passed through the subject P into an electrical signal, stores the electrical signal resulting from the converting process, and transmits the stored electrical signal to the image generating unit 24 (explained later).

The C-shaped arm 15 is an arm holding the X-ray tube 12, the X-ray beam limiting device 13, and the X-ray detector 16. The C-shaped arm 15 is configured so that the X-ray tube 12 and the X-ray beam limiting device 13 are positioned so as to oppose the X-ray detector 16, while the subject P is interposed therebetween.

The C-shaped arm rotating and moving mechanism 17 is a device used for rotating and moving the C-shaped arm 15. The top plate moving mechanism 18 is a device for moving the top plate 14.

The C-shaped-arm and top-plate mechanism controlling unit 19 adjusts rotation and movement of the C-shaped arm 15 and adjusts movement of the top plate 14, by controlling the C-shaped arm rotating and moving mechanism 17 and the top plate moving mechanism 18.

The beam-limiting controlling unit 20 controls a radiation range of the X-ray beams by adjusting an opening degree of the beam-limiting blades included in the X-ray beam limiting device 13.

The image generating unit 24 generates X-ray transmission images by using the electrical signal converted by the X-ray detector 16 from the X-ray beams that have passed through the subject P and stores the generated X-ray transmission images into the image storage unit 25.

The image storage unit 25 stores therein the X-ray transmission images that have been generated by the image generating unit 24. More specifically, the image storage unit 25 stores therein the X-ray transmission images that have been generated by the image generating unit 24, while keeping the X-ray transmission images in correspondence with times at which the images are taken.

The image processing unit 26 is a processing unit that performs various types of image processing procedures on the X-ray transmission images stored in the image storage unit 25. The image processing procedures performed by the image processing unit 26 will be explained in detail later.

The input unit 22 includes one or more of devices such as a mouse, a keyboard, a button, a trackball, and a joystick that are used by an operator like a medical doctor or a technologist who operates the X-ray diagnostic apparatus for the purpose of inputting various types of commands. The input unit 22 transfers the commands that have been received from the operator to the system controlling unit 21 (explained later).

The display unit 23 includes a monitor such as a liquid crystal display device or a Cathode-Ray Tube (CRT) display device. The display unit 23 displays, for example, a Graphical User Interface (GUI) for receiving the commands from the operator via the input unit 22, as well as the X-ray transmission images stored in the image storage unit 25 and X-ray transmission images resulting from the image processing procedures performed by the image processing unit 26.

The system controlling unit 21 controls an operation of the entirety of the X-ray diagnostic apparatus. In other words, based on the commands from the operator that have been transferred from the input unit 22, the system controlling unit 21 adjusts an X-ray dosage, exercises control to turn on and off the X-ray beam radiation, adjusts the rotation and the movement of the C-shaped arm 15, and adjusts the movement of the top plate 14, by controlling the high-voltage generator 11, the C-shaped-arm and top-plate mechanism controlling unit 19, and the beam-limiting controlling unit 20.

Further, based on the commands from the operator, the system controlling unit 21 controls the image generating unit 24 and the image processing unit 26. Furthermore, the system controlling unit 21 exercises control so that the GUI for receiving the commands from the operator, as well as the X-ray transmission images stored in the image storage unit 25 and the images resulting from the image processing procedures performed by the image processing unit 26 are displayed on the monitor included in the display unit 23.

Figure 2:
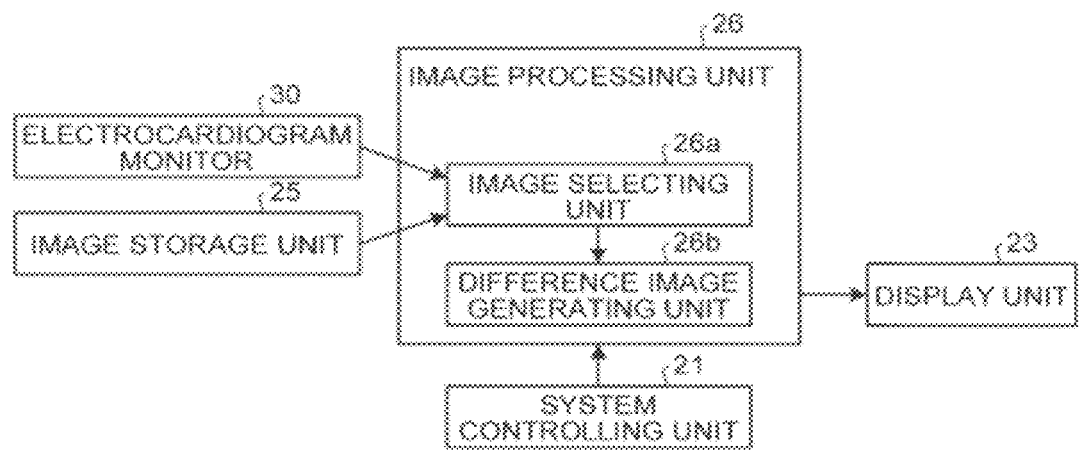
FIG. 2 is a drawing for explaining a configuration of an image processing unit according to the first embodiment.

An overall configuration of the X-ray diagnostic apparatus according to the first embodiment has been explained above. The X-ray diagnostic apparatus according to the first embodiment that is configured as described above generates X-ray transmission images by taking images of the heart of the subject P. More specifically, the X-ray diagnostic apparatus according to the first embodiment generates the X-ray transmission images by radiating the X-ray beams onto the heart of the subject P in which a contrast agent has been injected into the coronary arteries. Further, the X-ray diagnostic apparatus according to the first embodiment generates, through the image processing procedures performed by the image processing unit 26 explained below, X-ray transmission images with which it is possible to analyze the movement functions of the heart, while reducing a burden on the subject P. More specifically, the image processing unit 26 according to the first embodiment generates the X-ray transmission images with which it is possible analyze the movement functions of the heart, through a coronary angiography process. FIG. 2 is a drawing for explaining a configuration of the image processing unit according to the first embodiment.

As shown in FIG. 2, the image processing unit 26 according to the first embodiment includes an image selecting unit 26a and a difference image generating unit 26b.

The image selecting unit 26a selects X-ray transmission images to be used as processing targets of the difference image generating unit 26b, out of the X-ray transmission images stored in the image storage unit 25. For example, when the operator has input an image processing request via the input unit 22 after an X-ray transmission image taking process that uses a coronary angiography process has been finished, the system controlling unit 21 exercises control so that the image selecting unit 26a starts a process.

Figure 3:
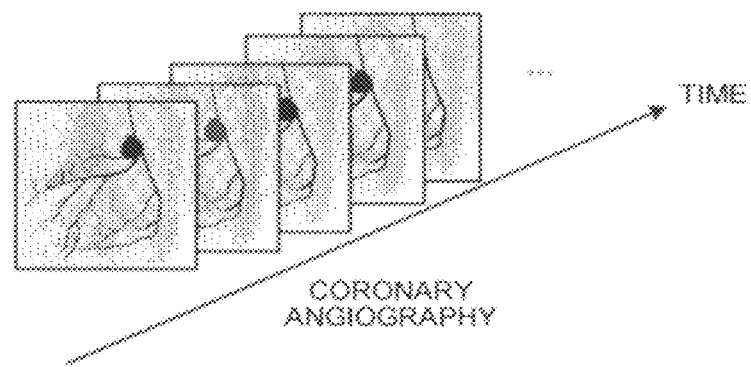
FIG. 3 is a drawing for explaining X-ray transmission images that can serve as selection targets of an image selecting unit.

FIG. 3 is a drawing for explaining the X-ray transmission images that can serve as the selection targets of the image selecting unit. As shown in FIG. 3, the image storage unit 25 stores therein a plurality of X-ray transmission images that have been obtained by taking, in a time sequence, images of the heart of the subject P in which a contrast agent has been injected into the coronary arteries during a coronary angiography process. Although not shown in FIG. 3, the image storage unit 25 also stores therein a plurality of X-ray transmission images obtained by taking images of the heart of the subject P before the coronary angiography process is performed.

The image selecting unit 26a selects first X-ray transmission images in each of which the myocardial tissue of the subject P is opacified, out of the plurality of X-ray transmission images as shown in FIG. 3 that are generated in the time sequence after the coronary angiography process has been performed. More specifically, the image selecting unit 26a selects the first X-ray transmission images, based on low-frequency components within the images. 4A, 4B and 4C are drawings for explaining the image selecting unit.

The contrast agent that has been injected into the coronary arteries flows into the vessels in the heart and subsequently flows into the intercellular substance in the myocardial tissue. Accordingly, as shown in FIG. 4A, after the coronary angiography process is performed, the degree of opacification of the vessels in the X-ray transmission images drastically rises along the time sequence from a point in time before the contrast agent is injected (see "TIME A" in the chart), reaches a peak (see "TIME B" in the chart), and subsequently falls. In contrast, as shown in FIG. 4A, after the coronary angiography process is performed, the degree of opacification of the myocardial tissue in the X-ray transmission images gradually rises after the degree of opacification of the vessels does, reaches a peak (see "TIME C" in the chart), and subsequently falls. In this situation, the peak value of the degree of opacification of the vessels is higher than the peak value of the degree of opacification of the myocardial tissue, as shown in FIG. 4A.

In this situation, the image selecting unit 26a extracts low-frequency components within the images by performing a Low Pass Filer (LPF) process on the plurality of X-ray transmission images arranged in the time sequence that are obtained after the coronary angiography has been performed. Further, the image selecting unit 26a selects the first X-ray transmission images in each of which the myocardial tissue of the subject is opacified, by selecting X-ray transmission images in each of which the extracted low-frequency component is equal to or larger than a predetermined threshold value.

In this situation, the image selecting unit 26a selects the plurality of first X-ray transmission images (i.e., a group of first X-ray transmission images) corresponding to one heart beat of the heart of the subject P, based on the times at which the X-ray transmission images have been taken and the electrocardiogram waveform of the subject P that has been obtained from the electrocardiogram monitor 30 together with the time information. In other words, as shown in FIG. 4A, the image selecting unit 26a selects the group of first X-ray transmission images corresponding to the one heart beat including a systolic phase and a diastolic phase.

Further, as shown in FIG. 4A, the image selecting unit 26a selects an X-ray transmission image generated immediately before the contrast agent is injected, as a second X-ray transmission image in which the myocardial tissue of the subject P is not opacified. Alternatively, the image selecting unit 26a may select, as the second X-ray transmission image, an X-ray transmission image obtained after the contrast agent flows out into the veins from the intercellular substance in the myocardia, among from the X-ray transmission images obtained after the coronary angiography process has been performed.

Figure 5A:
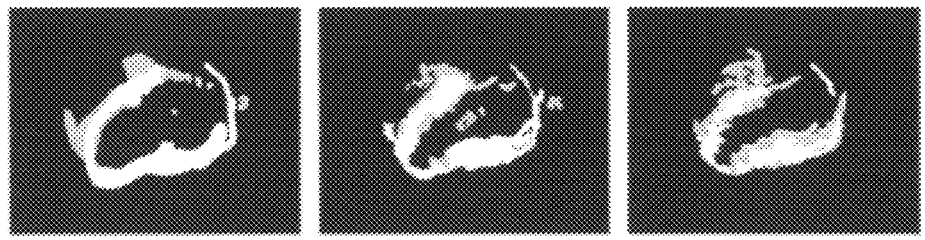
FIGS. 5A and 5B are drawings for explaining a difference image generating unit.
Figure 5B:
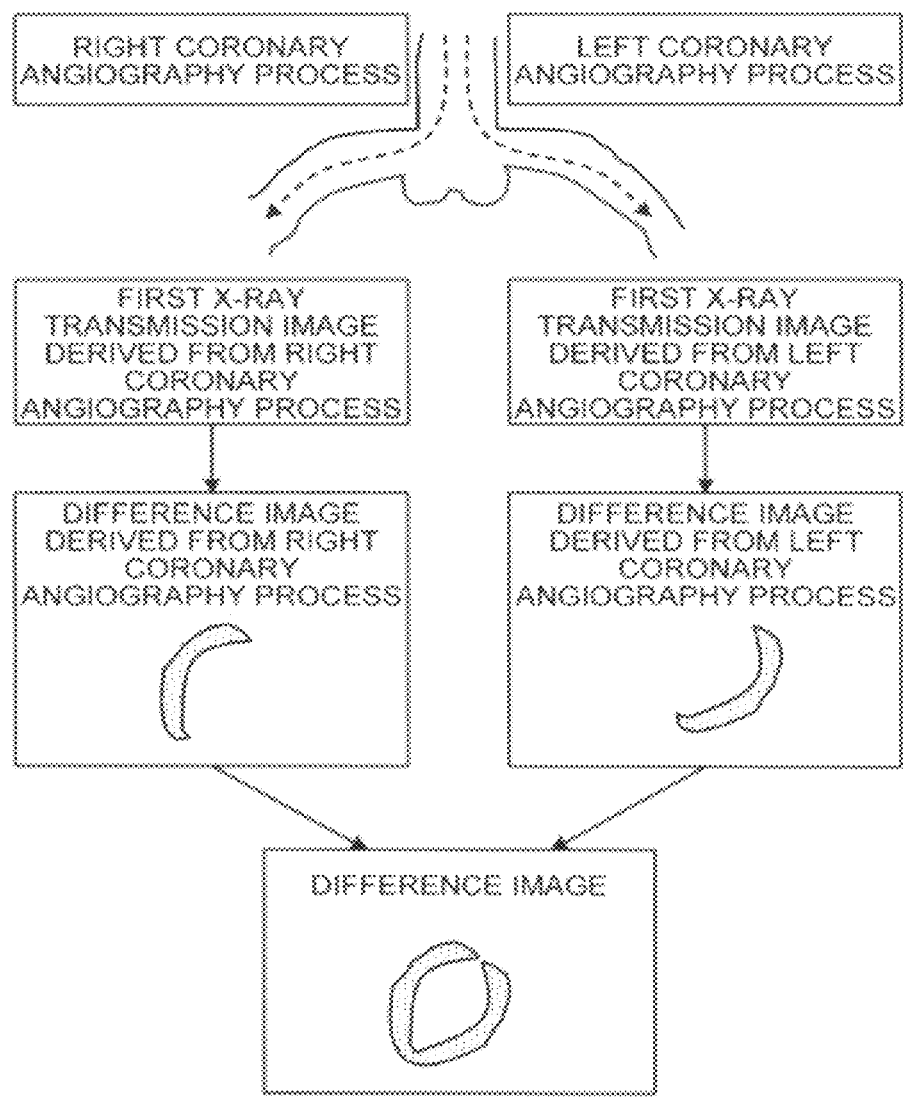

Returning to the description of FIG. 2, the difference image generating unit 26b generates difference images by calculating a difference in the second X-ray transmission image from each of the first X-ray transmission images. In other words, the difference image generating unit 26b generates the difference images in each of which the opacification of the myocardial tissue is highlighted, by calculating the difference in the second X-ray transmission image from each of the first X-ray transmission images, while using the second X-ray transmission image as a background image. FIGS. 5A and 5B are drawings for explaining the difference image generating unit.

More specifically, as shown in FIG. 5A, the difference image generating unit 26b generates the plurality of difference images by calculating the difference in the second X-ray transmission image from each member of the group of first X-ray transmission images corresponding to the one heart beat.

Further, the system controlling unit 21 shown in FIGS. 1 and 2 exercises control so that the display unit 23 displays the difference images that have been generated by the difference image generating unit 26b. More specifically, the system controlling unit 21 exercises control so that the display unit 23 displays the plurality of difference images (i.e., a group of difference images) that have been generated by the difference image generating unit 26b as moving pictures. Because the group of difference images in which substantially no vessels are rendered but the opacification of the myocardial tissue is highlighted is displayed as the moving pictures, medical doctors are able to view, in detail, the manner in which the myocardial tissue moves. Alternatively, according to a setting specified by the operator, the system controlling unit 21 may exercise control so that the display unit 23 displays the plurality of difference images side by side.

In the description above, the example has been explained in which the image selecting unit 26a selects the first X-ray transmission images, based on the low-frequency components within the images. According to the first embodiment, however, another arrangement is acceptable in which the image selecting unit 26a selects the first X-ray transmission images, based on elapsed time periods since the time at which the contrast agent is administered. More specifically, the image selecting unit 26a may select, as the group of first X-ray transmission images, a plurality of X-ray transmission images that have been generated within a predetermined time period including an elapsed time period that has been set by the operator in advance. For example, the operator sets an elapsed time period (corresponding to "TIME C" shown in FIG. 4A) with which the degree of opacification of the myocardial tissue is estimated to reach the peak as well as a predetermined time period "a". In this situation, the image selecting unit 26a selects, as the group of first X-ray transmission images, the plurality of X-ray transmission images that are generated between the time at which a time period "C−a" has elapsed since the administration of the contrast agent and the time at which a time period "C+a" has elapsed since the administration of the contrast agent. In this situation, if the operator makes an arrangement so that the time period "2×a" is equal to an average R-R interval of the subject P, the image selecting unit 26a is able to select the plurality of X-ray transmission images corresponding to one heart beat as the group of first X-ray transmission images.

Figure 4B:
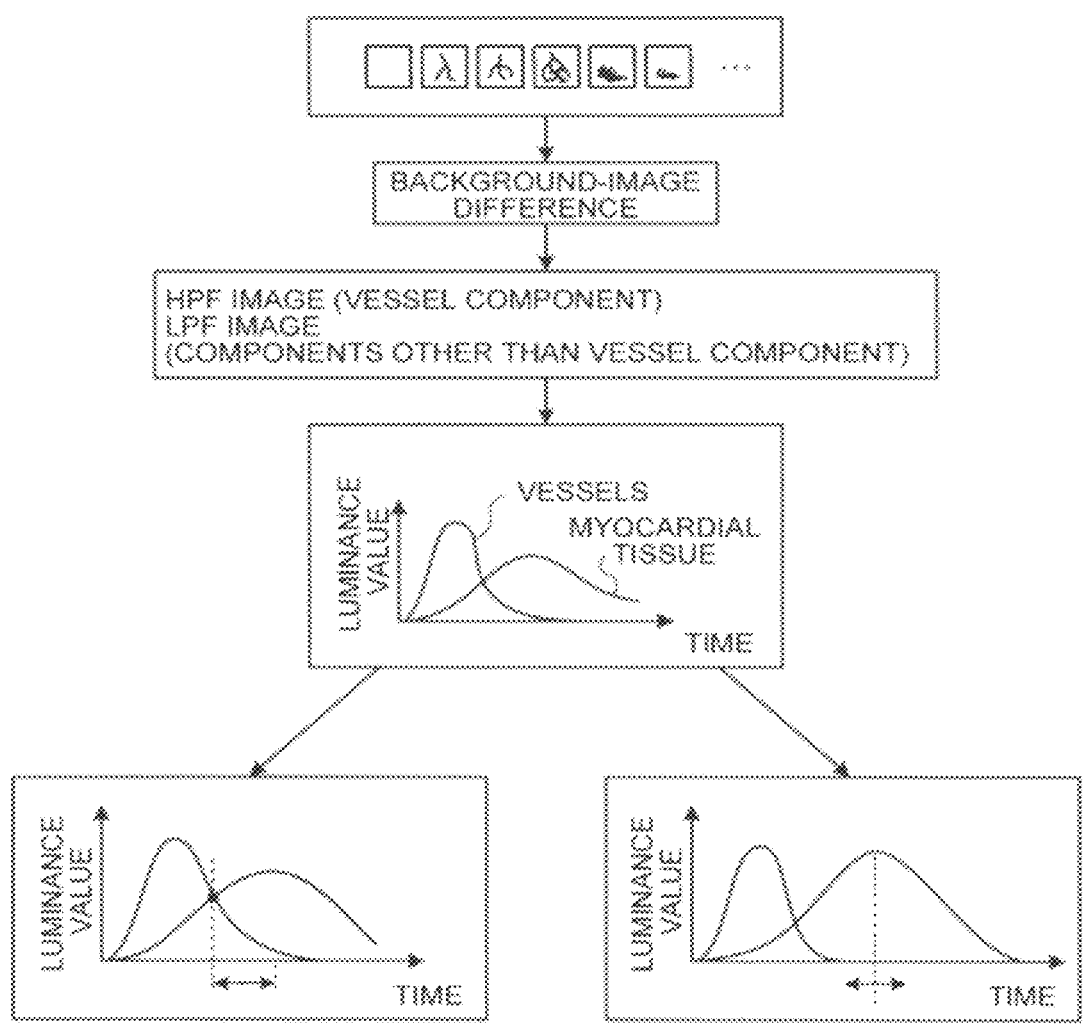

Alternatively, yet another arrangement is acceptable in which the image selecting unit 26a selects the first X-ray transmission images based on the low-frequency components as described above, by using the following method: The image selecting unit 26a selects the first X-ray transmission images based on images obtained by reducing the vessel component in each of a plurality of X-ray transmission images that have been taken in a time sequence during a coronary angiography process. More specifically, as shown in FIG. 4B, by calculating a background-image difference, the image selecting unit 26a eliminates components corresponding to the bones and the like from each member of the group of X-ray transmission images derived from the coronary angiography process. Further, as shown in FIG. 4B, the image selecting unit 26a generates High Pass Filter (HPF) images in each of which the vessel component is principally rendered, by performing an HPF process on each member of the group of X-ray transmission images derived from the coronary angiography process. Further, as shown in FIG. 4B, the image selecting unit 26a generates Low Pass Filter (LPF) images in each of which components other than the vessel component are principally rendered, by performing an LPF process on each member of the group of X-ray transmission images derived from the coronary angiography process. As a result, the LPF images are images in each of which the vessel component is reduced.

Further, as shown in FIG. 4B, the image selecting unit 26a generates a temporal change curve corresponding to changes in the density of the contrast agent in the vessels, by calculating an average luminance value for the entirety of each of the HPF images and an average luminance value for a region of interest that has been set in each of the HPF images and plotting the calculated average luminance values along a temporal axis. Similarly, as shown in FIG. 4B, the image selecting unit 26a generates a temporal change curve corresponding to changes in the density of the contrast agent in the myocardial tissue, by calculating an average luminance value for the entirety of each of the LPF images and an average luminance value for a region of interest that has been set in each of the LPF images and plotting the calculated average luminance values along a temporal axis. To set a region of interest in an LPF image, for example, the image selecting unit 26a determines a center of gravity based on the luminance values of the pixels in the LPF image. Further, for example, while using the determined center of gravity as the center of a circle, the image selecting unit 26a sets the circle of which the diameter is equal to a half of the image size, as the region of interest.

Further, as shown in FIG. 4B, the image selecting unit 26a selects, as the group of first X-ray transmission images, a group of X-ray transmission images from the point in time when the temporal change curve of the myocardial tissue intersects the temporal change curve of the vessels, to the point in time corresponding to one heart beat later. Alternatively, an arrangement is acceptable in which, as shown in FIG. 4B, the image selecting unit 26a selects, as the group of first X-ray transmission images, a group of X-ray transmission images that correspond to the duration of one heart beat and are positioned on either side of the point in time when the luminance value reaches a peak in the temporal change curve of the myocardial tissue. In the case where the group of first X-ray transmission images is selected by using only the temporal change curve of the myocardial tissue, another arrangement is acceptable in which the image selecting process is performed by generating only the LPF images.

As explained above, to generate the difference images in each of which the opacification of the myocardial tissue is highlighted from the group of X-ray transmission images taken during a coronary angiography process that is performed for the purpose of opacifying the vessels, it is desirable to select the group of first X-ray transmission images by using the LPF images in each of which the vessel component is reduced.

Figure 4C:
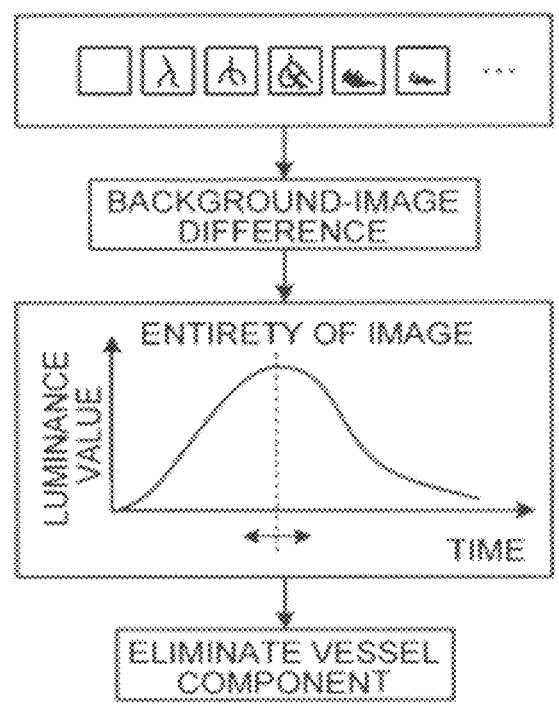

Further, according to the first embodiment, another arrangement is acceptable in which the image selecting unit 26a selects the first X-ray transmission images based on an average luminance value for the entirety of each of images. More specifically, as shown in FIG. 4C, by calculating a background-image difference, the image selecting unit 26a eliminates components corresponding to the bones and the like from each member of the group of X-ray transmission images derived from the coronary angiography process. Subsequently, the image selecting unit 26a calculates an average luminance value for the entirety of the image, for each of the images for which the background-image difference has been calculated. After that, as shown in FIG. 4C, the image selecting unit 26a generates a temporal change curve by plotting the average luminance values for the entirety of the images along a temporal axis. In this situation, when the volume of the vessels in the heart is compared with the volume of the myocardial tissue in the heart, the latter is larger than the former. Accordingly, it is presumed that, in the X-ray transmission image at the point in time when the average luminance value for the entirety of the image reaches the peak, the myocardial tissue is principally opacified. For this reason, as shown in FIG. 4C, for example, the image selecting unit 26a selects the group of X-ray transmission images that correspond to the duration of one heart beat and are positioned on either side of the point in time when the average luminance value for the entirety of the image reaches the peak. Further, as shown in FIG. 4C, the image selecting unit 26a generates a group of LPF images obtained by eliminating the vessel component from each member of the group of X-ray transmission images that has been selected based on the average luminance values of the entirety of the images and uses the generated group of LPF images as the group of first X-ray transmission images.

Alternatively, yet another arrangement is acceptable in which the image selecting unit 26a selects the group of X-ray transmission images that correspond to the duration of one heart beat and are positioned on either side of the point in time when the average luminance value for the entirety of the image reaches the peak, as the group of first X-ray transmission images.

Further, the group of difference images shown in FIG. 5A may be generated by performing the coronary angiography process twice. The coronary arteries can be roughly divided into the left coronary artery and the right coronary artery. Also, the myocardial tissue can be roughly divided into a myocardial tissue that is nourished by the left coronary artery and a myocardial tissue that is nourished by the right coronary artery. Accordingly, to generate, without fail, the difference images in each of which the opacification of the entirety of the myocardial tissue is highlighted, it is desirable, in some situations, to perform a left coronary angiography process and a right coronary angiography process in two separate processes, as shown in FIG. 5B.

In those situations, as shown in FIG. 5B, the image selecting unit 26a selects an X-ray transmission image in which the myocardial tissue nourished by the left coronary artery is opacified, out of a plurality of X-ray transmission images taken by performing a left coronary angiography process, as a "first X-ray transmission image derived from the left coronary angiography process". More specifically, the image selecting unit 26a selects a "group of first X-ray transmission images derived from the left coronary angiography process" corresponding to one heart beat. In addition, as shown in FIG. 5B, the image selecting unit 26a selects an X-ray transmission image in which the myocardial tissue nourished by the right coronary artery is opacified, out of a plurality of X-ray transmission images taken by performing a right coronary angiography process, as a "first X-ray transmission image derived from the right coronary angiography process". More specifically, the image selecting unit 26a selects a "group of first X-ray transmission images derived from the right coronary angiography process" corresponding to one heart beat. It should be noted that, to select the "first X-ray transmission image derived from the left coronary angiography process" and the "first X-ray transmission image derived from the right coronary angiography process", a method that is specified from among the methods described above is used.

Further, the difference image generating unit 26b generates, as shown in FIG. 5B, a difference image derived from the left coronary angiography process and a difference image derived from the right coronary angiography process by calculating differences in the second X-ray transmission image from the first X-ray transmission image derived from the left coronary angiography process and from the first X-ray transmission image derived from the right coronary angiography process. Further, the difference image generating unit 26b generates a difference image by combining together the two difference images that have been generated. More specifically, the difference image generating unit 26b generates the difference image by combining together the difference image derived from the left coronary angiography process and the difference image derived from the right coronary angiography process that are in mutually the same cardiac phase.

Further, in the description above, the example has been explained in which the image selecting unit 26a selects the first X-ray transmission images corresponding to the one heart beat. According to the first embodiment, however, another arrangement is acceptable in which the image selecting unit 26a selects first X-ray transmission images corresponding to two or more heart beats. Further, according to the first embodiment, yet another arrangement is acceptable in which the image selecting unit 26a selects a plurality of first X-ray transmission images in each of which the myocardial tissue of the subject P is opacified, regardless of the cardiac phases of the subject P. Even in this situation, the difference image generating unit 26b generates a plurality of difference images by calculating a difference in the second X-ray transmission image from each of the plurality of first X-ray transmission images, and also, the system controlling unit 21 exercises control so that the display unit 23 displays the plurality of difference images as moving pictures or side by side.

Further, in the description above, the example has been explained in which the image selecting unit 26a selects the plurality of first X-ray transmission images. According to the first embodiment, however, yet another arrangement is acceptable in which the image selecting unit 26a selects one first X-ray transmission image. In this situation, the difference image generating unit 26b generates one difference image by calculating a difference in the second X-ray transmission image from the one first X-ray transmission image, and also, the system controlling unit 21 exercises control so that the display unit 23 displays the one difference image.

Further, in the description above, the example has been explained in which the image selecting unit 26a selects the second X-ray transmission image. According to the first embodiment, however, yet another arrangement is acceptable in which the operator selects the second X-ray transmission image. Furthermore, in the description above, the example has been explained in which the image selecting unit 26a selects the first X-ray transmission images. According to the first embodiment, however, yet another arrangement is acceptable in which the operator selects the first X-ray transmission images.

In the case where the operator selects the X-ray transmission images used in the process performed by the difference image generating unit 26b, the system controlling unit 21 reads, in response to a request from the operator, the plurality of X-ray transmission images stored in the image storage unit 25 so that the display unit 23 displays the read images. Subsequently, by using the mouse or the like included in the input unit 22, the operator selects X-ray transmission images in each of which the myocardial tissue is opacified as the first X-ray transmission images and also selects an X-ray transmission image in which the myocardial tissue is not opacified as the second X-ray transmission image, out of the plurality of X-ray transmission images displayed by the display unit 23. Subsequently, the system controlling unit 21 transfers the X-ray transmission images that have been selected by the operator as the first X-ray transmission images as well as the X-ray transmission image that has been selected by the operator as the second X-ray transmission image, to the difference image generating unit 26b. After that, the system controlling unit 21 causes the display unit 23 to display the difference images that have been generated by the difference image generating unit 26b.

Next, a process performed by the X-ray diagnostic apparatus according to the first embodiment will be explained, with reference to FIG. 6. FIG. 6 is a flowchart for explaining the process performed by the X-ray diagnostic apparatus according to the first embodiment. With reference to FIG. 6, a process that is performed after X-ray transmission images have been taken by performing a coronary angiography process and a plurality of X-ray transmission images have been stored into the image storage unit 25 will be explained.

As shown in FIG. 6, the X-ray diagnostic apparatus according to the first embodiment judges whether an image processing request has been received from the operator via the input unit 22 (step S101). In this situation, in the case where no image processing request has been received (step S101: No), the X-ray diagnostic apparatus is in a stand-by state. On the contrary, in the case where an image processing request has been received (step S101: Yes), the image selecting unit 26a selects a group of first X-ray transmission images in which the myocardial tissue of the subject P is opacified as well as a second X-ray transmission image in which the myocardial tissue of the subject P is not opacified (step S102). More specifically, the image selecting unit 26a selects the plurality of first X-ray transmission images in each of which the myocardial tissue of the subject P is opacified, out of the X-ray transmission images stored in the image storage unit 25, based on low-frequency components within the images. Even more specifically, the image selecting unit 26a selects the plurality of first X-ray transmission images corresponding to one heart beat of the heart of the subject P, based on the times at which the X-ray transmission images have been taken and the electrocardiogram waveform of the subject P that has been obtained from the electrocardiogram monitor 30 together with the time information.

Further, the difference image generating unit 26b generates a group of difference images by calculating a difference in the second X-ray transmission image from each member of the group of first X-ray transmission images (step S103). After that, the system controlling unit 21 exercises control so that the display unit 23 displays the group of difference images (step S104), and the process is ended.

As explained above, according to the first embodiment, the difference image generating unit 26b generates the difference images by calculating the difference in the second X-ray transmission image from each of the first X-ray transmission images, the second X-ray transmission image being an image in which the myocardial tissue of the subject P is not opacified and the first X-ray transmission images each being an image in which the myocardial tissue of the subject P is opacified with the contrast agent that has been injected into the coronary arteries. Further, the system controlling unit 21 exercises control so that the display unit 23 displays the difference images that have been generated by the difference image generating unit 26b.

In other words, according to the first embodiment, because the difference images in each of which the opacification of the myocardial tissue is highlighted are generated and displayed, medical doctors are able to make a diagnosis regarding the movement functions of the heart, by referring to the difference images in each of which the myocardial tissue is rendered. Further, according to the first embodiment, the difference images are generated by performing only the coronary angiography process, without the need to perform an LVG process. Thus, it is possible to avoid injecting a large amount of contrast agent. In addition, it is possible to reduce X-ray exposure amount. Further, because only the coronary angiography process is performed according to the first embodiment, there is no need to insert an LVG-purpose catheter into the subject after the coronary-angiography-purpose catheter has been removed. Thus, it is possible to shorten the time period required to perform the examination. Furthermore, according to the first embodiment, by performing only the coronary angiography process, it is possible to make a diagnosis regarding vessel stenosis at the same time when the movement functions of the heart are analyzed. Thus, according to the first embodiment, it is possible to generate the X-ray transmission images with which it is possible to analyze the movement functions of the heart, while reducing the burden on the subject P.

Furthermore, according to the first embodiment, the difference image generating unit 26b generates the plurality of difference images from the plurality of first X-ray transmission images, respectively, so that the system controlling unit 21 exercises control in such a manner that the display unit 23 displays the plurality of difference images that have been generated by the difference image generating unit 26b as the moving pictures or side by side. With this arrangement according to the first embodiment, medical doctors are able to analyze the manner in which the myocardial tissue moves along with the pulsation. In particular, because the plurality of difference images in each of which substantially no vessels are rendered but the opacification of the myocardial tissue is highlighted are displayed as the moving pictures, medical doctors are able to view, in detail, the manner in which the myocardial tissue moves.

Furthermore, according to the first embodiment, the image selecting unit 26a selects the first X-ray transmission images, out of the plurality of X-ray transmission images that have been taken in the time sequence by performing the coronary angiography process, based on the low-frequency components within the images. Subsequently, the difference image generating unit 26b generates the difference images from the first X-ray transmission images that have been selected by the image selecting unit 26a. With this arrangement according to the first embodiment, it is possible to automatically perform the process to select the first X-ray transmission images and thus reduce burdens on the medical doctors.

Furthermore, according to the first embodiment, the image selecting unit 26a selects the plurality of first X-ray transmission images corresponding to at least one heart beat of the heart of the subject P. With this arrangement according to the first embodiment, because the group of difference images corresponding to the one heart beat is displayed as the moving pictures or side by side, medical doctors are able to analyze, in detail, the manner in which the myocardial tissue moves along with the pulsation. In particular, because the group of difference images corresponding to the one heart beat in which substantially no vessels are rendered but the opacification of the myocardial tissue is highlighted is displayed as the moving pictures, medical doctors are able to view, in detail, the manner in which the myocardial tissue moves for the duration of the one heart beat.

The difference images described above are also useful in, for example, treatments for arrhythmia that use a catheter ablation process. The catheter ablation process is a method for curatively treating arrhythmia by cauterizing the myocardia by causing a high-frequency electric current to flow from a tip end of a catheter, while the catheter inserted into the heart via vessels is in contact with the myocardium causing arrhythmia. There are situations, however, in which it is difficult to determine whether the catheter is in contact with the myocardium causing the arrhythmia, even by referring to an X-ray transmission image that is displayed in a real-time manner while such a catheter ablation process is being performed. To cope with these situations, the difference images that have been generated can be displayed in combination with the X-ray transmission image that is displayed in a real-time manner while the catheter ablation process is being performed. With this arrangement, medical doctors are able to bring, without fail, the catheter into contact with the myocardium causing arrhythmia. In other words, by using the difference images, it is possible to improve the level of precision in the treatments for arrhythmia.

Furthermore, the difference images described above are also useful in regenerative medicine. Recent developments in regenerative medicine techniques have made it possible to regenerate an infarct region in a myocardium by directly administering a stem cell or a cell growth factor into the myocardium. As an example of a method for administering a stem cell or a cell growth factor, a method has been proposed by which a tube-like device like a catheter is used for administering the substance from the exterior of the body of the subject. According to this method, a tip end of such a tube-like device needs to be in contact with the infarction site of the myocardium without fail. In this situation, like the example of the catheter ablation process described above, by having the difference images displayed in combination with an X-ray transmission image, medical doctors are able to bring, without fail, the tube-like device into contact with the infarction site of the myocardium.

In detail, the difference images described above is used to visualize the myocardium. Three territories are defined; normal territory, infarct territory, and border zone. Normal territory shows normal intensity and normal motion in the difference image. Infarct territory shows thinned intensity and is akinetic. Border zone is surrounding the infarct. Then, catheter is inserted into left venticular and cells are injected from the tip of catheter to the infarct territory and border zone by referring the difference images.

As a second embodiment, an example in which the shape of the myocardial tissue rendered in each of the difference images is highlighted and displayed will be explained, with reference to FIGS. 7 and 8. FIG. 7 is a drawing for explaining a configuration of an X-ray diagnostic apparatus according to the second embodiment. FIGS. 8A and 8B are drawings for explaining a tracing unit.

To begin the explanation, as shown in FIG. 7, the image processing unit 26 according to the second embodiment is different from the image processing unit 26 according to the first embodiment explained with reference to FIG. 2 in that a tracing unit 26c is further included therein. In the following sections, the second embodiment will be explained while a focus is placed on this constituent element. The processes performed by the image selecting unit 26a and the difference image generating unit 26b shown in FIG. 7 are the same as the processes explained in the description of the first embodiment. Thus, the explanation thereof will be omitted.

Based on pixel values of the pixels included in each of the difference images that have been generated by the difference image generating unit 26b, the tracing unit 26c generates a curve obtained by tracing an outline of a high-luminance region rendered in the difference image. For example, the tracing unit 26c generates the curve obtained by tracing the outline of the high-luminance region, as shown in FIG. 8A, by extracting a region defined by pixels of which the pixel value is equal to or higher than a predetermined value, as the high-luminance region. In this situation, in the case where a plurality of difference images have been generated, the tracing unit 26c generates a curve obtained by tracing an outline of a high-luminance region in each of the difference images.

More specifically, the tracing unit 26c generates the curve by tracing the shape of the myocardial tissue that has been opacified by the contrast agent. In the case where, as explained with reference to FIG. 5B, a left coronary angiograph process and a right coronary angiography process have been performed in two separate processes, the tracing unit 26c generates the curve obtained by tracing the shape of the entirety of the myocardial tissue that has been opacified by the contrast agent, by performing the following process: The tracing unit 26c generates the curve obtained by tracing the shape of the entirety of the myocardial tissue that has been opacified by the contrast agent, from a difference image that has been generated by combining a difference image derived from the left coronary angiography process with a difference image derived from the right coronary angiography process. Alternatively, the tracing unit 26c generates the curve obtained by tracing the shape of the entirety of the myocardial tissue that has been opacified by the contrast agent, by generating a curve obtained by tracing the outline of a high-luminance region rendered in a difference image derived from the left coronary angiography process and a curve obtained by tracing the outline of a high-luminance region rendered in a difference image derived from the right coronary angiography process and further combining together the two curves that have been generated.

In this situation, there is a possibility that, as a result of the tracing process performed by the tracing unit 26c, a region in which the aortic valve is positioned may not be traced, as shown in FIG. 8A. In that situation, the tracing unit 26c generates a curve by combining an image in which the vessels are opacified with a difference image. In other words, as shown in FIG. 8B, the tracing unit 26c generates a combined image by combining the difference image in which the myocardial tissue is highlighted with an X-ray transmission image (i.e., an image in which the vessels are easily observed) taken by performing a normal coronary angiography process. Further, as shown in FIG. 8B, the tracing unit 26c performs a tracing process by using the combined image. As a result, as shown in FIG. 8B, the tracing unit 26c is able to generate the curve from which it is possible to easily understand the position of the aortal valve that is positioned at the end of the left ventricle. In other words, by using the image in which the vessels are opacified, the tracing unit 26c is able to generate, without fail, the curve obtained by tracing the shape of the entirety of the myocardial tissue.

Subsequently, the system controlling unit 21 exercises control so that the display unit 23 further displays the curve generated by the tracing unit 26c together with the difference image. In other words, the system controlling unit 21 exercises control so that the difference image in which the curve obtained by tracing the outline of the high-luminance region is rendered is displayed. More specifically, the system controlling unit 21 exercises control so that a plurality of difference images in each of which the curve obtained by tracing the outline of the high-luminance region is rendered are displayed as moving pictures. Alternatively, the system controlling unit 21 may exercise control so that the plurality of difference images in each of which the curve obtained by tracing the outline of the high-luminance region is rendered are displayed side by side.

In the description above, the example has been explained in which the tracing unit 26c automatically performs the tracing process. According to the second embodiment, however, another arrangement is acceptable in which the operator sets a curve obtained by tracing the outline of the high-luminance region in each of the difference images, by using a rendering function included in the image processing unit 26.

Next, a process performed by the X-ray diagnostic apparatus according to the second embodiment will be explained, with reference to FIG. 9. FIG. 9 is a flowchart for explaining the process performed by the X-ray diagnostic apparatus according to the second embodiment. With reference to FIG. 9, a process that is performed after X-ray transmission images have been taken by performing a coronary angiography process and a plurality of X-ray transmission images have been stored into the image storage unit 25 will be explained.

As shown in FIG. 9, the X-ray diagnostic apparatus according to the second embodiment judges whether an image processing request has been received from the operator via the input unit 22 (step S201). In this situation, in the case where no image processing request has been received (step S201: No), the X-ray diagnostic apparatus is in a stand-by state. On the contrary, in the case where an image processing request has been received (step S201: Yes), the image selecting unit 26a selects a group of first X-ray transmission images in which the myocardial tissue of the subject P is opacified as well as a second X-ray transmission image in which the myocardial tissue of the subject P is not opacified (step S202).

Further, the difference image generating unit 26b generates a group of difference images by calculating a difference in the second X-ray transmission image from each member of the group of first X-ray transmission images (step S203). After that, the tracing unit 26c generates a curve obtained by tracing the outline of the high-luminance region in each member of the group of difference images (step S204).

Further, the system controlling unit 21 exercises control so that the display unit 23 displays the group of difference images in which results of the tracing process are rendered (step S205), and the process is ended.

As explained above, according to the second embodiment, based on the pixel values of the pixels included in each of the difference images that have been generated by the difference image generating unit 26b, the tracing unit 26c generates the curve obtained by tracing the outline of the high-luminance region rendered in the difference image. Subsequently, the system controlling unit 21 exercises control so that the display unit 23 displays the curves generated by the tracing unit 26c, together with the difference images.

In other words, according to the second embodiment, because the result of tracing the high-luminance region within each of the difference images is further displayed, medical doctors are able to clearly view the shape of the myocardial tissue that has been opacified with the contrast agent. Further, according to the second embodiment, because the tracing process can automatically be performed, it is possible to reduce burdens on the medical doctors.

Figure 10:
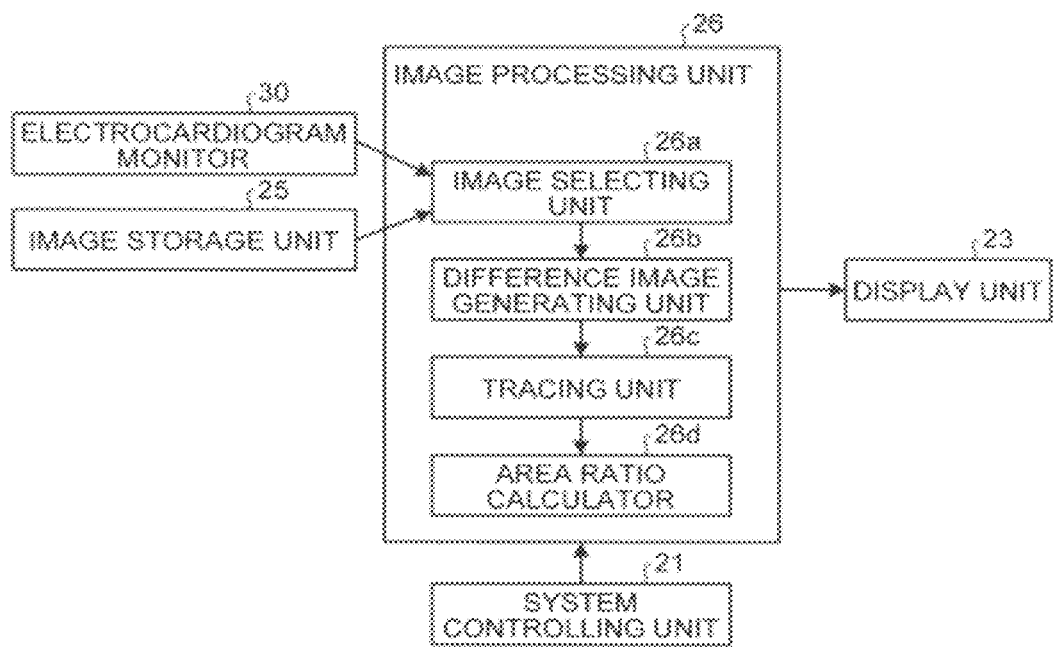
FIG. 10 is a drawing for explaining a configuration of an X-ray diagnostic apparatus according to a third embodiment.
Figure 11:
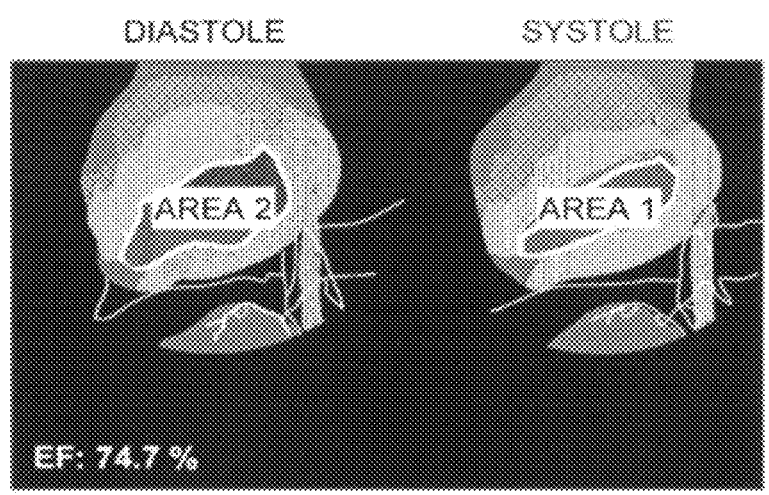
FIGS. 11 and 12 are drawings for explaining an area ratio calculator.
Figure 12:
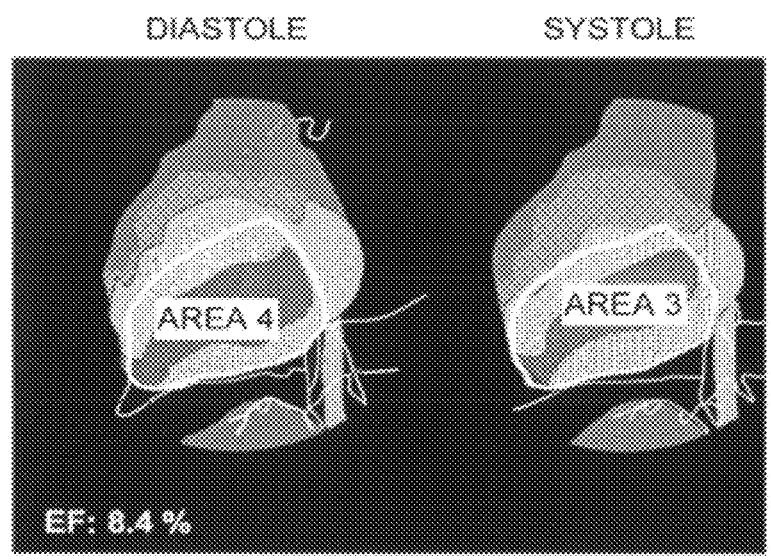

As a third embodiment of the present invention, an example in which an index value is calculated for quantitatively analyzing the movement functions of the heart by using the difference images will be explained, with reference to FIGS. 10 to 12. FIG. 10 is a drawing for explaining a configuration of an X-ray diagnostic apparatus according to the third embodiment. FIGS. 11 and 12 are drawings for explaining an area ratio calculator.

To begin the explanation, as shown in FIG. 10, the image processing unit 26 according to the third embodiment is different from the image processing unit 26 according to the second embodiment explained with reference to FIG. 7 in that an area ratio calculator 26d is further included therein. In the following sections, the third embodiment will be explained while a focus is placed on this constituent element. The processes performed by the image selecting unit 26a and the difference image generating unit 26b shown in FIG. 10 are the same as the processes explained in the description of the first embodiment, whereas the process performed by the tracing unit 26c shown in FIG. 10 is the same as the process explained in the description of the second embodiment. Thus, the explanation thereof will be omitted.

The area ratio calculator 26d calculates an index value (i.e., an area ratio) corresponding to an Ejection Fraction (EF), by using results of the process performed by the tracing unit 26c on difference images. More specifically, the area ratio calculator 26d performs the process to calculate the area ratio by using the curves that have been generated by the tracing unit 26c with respect to a difference image during a systolic phase (hereinafter, "the systole") and a difference image during a diastolic phase (hereinafter, "the diastole"), among from the group of difference images corresponding to one heart beat that has been generated from the group of first X-ray transmission images corresponding to the one heart beat. It is desirable that the process to calculate the area ratio is performed by using a difference image during end systole and a difference image during end diastole.

More specifically, the area ratio calculator 26d calculates an area (i.e., an area 1) of a region defined by a curve obtained by tracing the inside of an outline of a high-luminance region rendered in the difference image during the systole. Further, the area ratio calculator 26d calculates an area (i.e., an area 2) of a region defined by a curve obtained by tracing the inside of the outline of the high-luminance region rendered in the difference image during the diastole. Subsequently, the area ratio calculator 26d calculates an area ratio between the area 1 and the area 2 by calculating "100×(the area 2−the area 1)/the area 2". In this situation, the curve obtained by tracing the inside of the outline of the high-luminance region rendered in the difference image during the systole is a curve that substantially corresponds to the inside of the heart wall during the systole, whereas the curve obtained by tracing the inside of the outline of the high-luminance region rendered in the difference image during the diastole is a curve that substantially corresponds to the inside of the heart wall during the diastole. Accordingly, the area ratio between the area 1 and the area 2 serves as an index value corresponding to an EF that has conventionally been calculated from an X-ray transmission image taken by performing an LVG process.

Further, the area ratio calculator 26d calculates an area (i.e., an area 3) of a region defined by a curve obtained by tracing the outside of the outline of the high-luminance region rendered in the difference image during the systole. In addition, the area ratio calculator 26d calculates an area (i.e., an area 4) of a region defined by a curve obtained by tracing the outside of the outline of the high-luminance region rendered in the difference image during the diastole. Subsequently, the area ratio calculator 26d calculates an area ratio between the area 3 and the area 4 by calculating "100×(the area 4−the area 3)/the area 4". In this situation, the curve obtained by tracing the outside of the outline of the high-luminance region rendered in the difference image during the systole is a curve that substantially corresponds to the outside of heart wall during the systole, whereas the curve obtained by tracing the outside of the outline of the high-luminance region rendered in the difference image during the diastole is a curve that substantially corresponds to the outside of the heart wall during the diastole. Accordingly, the area ratio between the area 3 and the area 4 serves as a new index value indicating the manner in which the outside of the heart wall moves along with the pulsation. As explained above, the area ratio calculator 26d calculates the two area ratios corresponding to the EF of the inside of the heart wall and the EF of the outside of the heart wall, as index values used for analyzing the manner in which the heart moves along with the pulsation.

For example, as shown in FIG. 11, the area ratio calculator 26*d* calculates the area 1 from a result of the tracing process performed on the difference image during the systole and calculates the area 2 from a result of the tracing process performed on the difference image during the diastole. Subsequently, the area ratio calculator 26*d* calculates "100×(the area 2–the area 1)/the area 2=74.7%", as shown in FIG. 11.

Further, as shown in FIG. 12, the area ratio calculator 26*d* calculates the area 3 from a result of the tracing process performed on the difference image during the systole and calculates the area 4 from a result of the tracing process performed on the difference image during the diastole. Subsequently, the area ratio calculator 26*d* calculates "100×(the area 4–the area 3)/the area 4=8.4%", as shown in FIG. 12.

The system controlling unit 21 exercises control so that the display unit 23 displays the two area ratios that have been calculated by the area ratio calculator 26*d*. With this arrangement, medical doctors are able to confirm, for example, that the heart is in a state of having normal movement because the area ratio between the area 1 and the area 2 is "74.7%", and the inside of the heart wall contracts normally along with the pulsation. In addition, medical doctors are able to confirm that the heart is in a state of having normal movement because the area ratio between the area 3 and the area 4 is "8.4%", and the outside of the heart wall moves only slightly along with the pulsation.

Alternatively, another arrangement is acceptable in which the area ratio calculator 26*d* calculates a new index value from the areas that have been calculated to calculate the area ratios. More specifically, the area ratio calculator 26*d* may calculate, as the new index value, an area of the region defined by the outlines of the high-luminance regions rendered in difference images. Even more specifically, the area ratio calculator 26*d* may calculate an area obtained by subtracting the area 1 from the area 2 as an index value indicating the manner in which the inside of the heart wall contracts. Further, the area ratio calculator 26*d* may calculate an area obtained by subtracting the area 3 from the area 4 as an index value indicating the manner in which the outside of the heart wall contracts. Alternatively, the area ratio calculator 26*d* may calculate an area obtained by subtracting the area 2 from the area 4 as an index value indicating the size of the myocardial tissue during the diastole. Further, the area ratio calculator 26*d* may calculate an area obtained by subtracting the area 1 from the area 3 as an index value indicating the size of the myocardial tissue during the systole. Further, another arrangement is acceptable in which a plurality of areas indicating the contraction of the heart wall or a plurality of areas indicating the size of the myocardial tissue are calculated from, for example, a plurality of difference images corresponding to one heart beat. Further, yet another arrangement is acceptable in which the area ratio calculator 26*d* calculates an index value indicating the contraction of the heart wall or the size of the myocardial tissue by converting the calculated area into volume.

Figure 13:
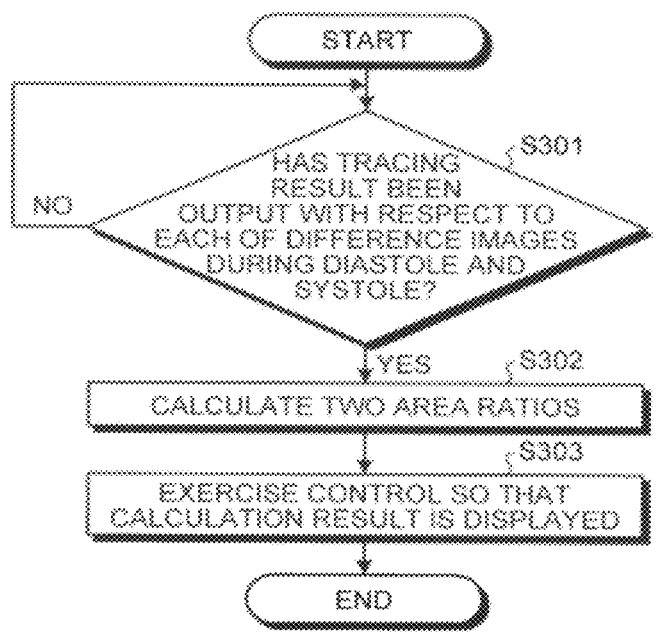
FIG. 13 is a flowchart for explaining a process performed by the X-ray diagnostic apparatus according to the third embodiment.

Next, a process performed by the X-ray diagnostic apparatus according to the third embodiment will be explained, with reference to FIG. 13. FIG. 13 is a flowchart for explaining the process performed by the X-ray diagnostic apparatus according to the third embodiment. With reference to FIG. 13, a process that is performed after the tracing unit 26*c* has generated the curve obtained by tracing the outline of the high-luminance region with respect to each member of the group of difference images corresponding to one heart beat will be explained.

As shown in FIG. 13, the X-ray diagnostic apparatus according to the third embodiment judges whether a result of the tracing process has been output with respect to each of the difference images during the systole and the diastole (step S301). In this situation, in the case where the tracing results have not been output (step S301: No), the X-ray diagnostic apparatus is in a stand-by state. On the contrary, in the case where the tracing results have been output (step S301: Yes), the area ratio calculator 26*d* calculates the two area ratios from the tracing results (step S302). In other words, the area ratio calculator 26*d* calculates "100×(the area 2–the area 1)/the area 2" and "100×(the area 4–the area 3)/the area 4".

Subsequently, the system controlling unit 21 exercises control so that the display unit 23 displays a result of the calculating process performed by the area ratio calculator 26*d* (step S303), and the process is ended.

As explained above, according to the third embodiment, the area ratio calculator 26*d* performs the process of calculating the area ratios by using the curves that have been generated by the tracing unit 26*c* with respect to the difference image during the systole and the difference image during the diastole, among from the group of difference images corresponding to one heart beat that have been generated from the group of first X-ray transmission images corresponding to the one heart beat. In other words, by using the results of the tracing process performed on the difference image during the systole and the difference image during the diastole, the area ratio calculator 26*d* calculates the two area ratios corresponding to the EF of the inside of the heart wall and the EF of the outside of the heart wall, as the index values used for analyzing the manner in which the heart moves along with the pulsation. With this arrangement according to the third embodiment, it is possible to provide medical doctors with the values with which it is possible to objectively evaluate the movement functions of the heart by performing only the coronary angiography process.

Another arrangement is acceptable in which the area ratio calculator 26*d* performs only the process of calculating the area ratio by using the curves obtained by tracing the inside of the outline of the high-luminance region. Further, the area ratio calculator 26*d* may perform the process of calculating the area ratio by using the results of the tracing process performed by the tracing unit 26*c*, as explained above, or may perform the process of calculating the area ratio by using results of a tracing process performed by the operator on the outline of the high-luminance region in the difference images.

Further, yet another arrangement is acceptable in which a plurality of area ratios corresponding to the EF of the inside of the heart wall are calculated for mutually different cardiac phases, by using the area 2 in a difference image during end diastole and areas of regions each of which is defined by a curve on the inside of the outline within a different member of the group of difference images corresponding to one heart beat. Similarly, yet another arrangement is acceptable in which a plurality of area ratios corresponding to the EF of the outside of the heart wall are calculated for mutually different cardiac phases, by using the area 4 in a difference image during end diastole and areas of regions each of which is defined by a curve on the outside of the outline within a different member of the group of difference images corresponding to one heart beat.

In the description above, the example has been explained in which the process to calculate the area ratios is performed by using the results obtained by tracing the high-luminance region. According to the third embodiment, however, the process to calculate the area ratios may be performed by using a method by which a plurality of points are tracked, as explained below. According to this method, for example, the plurality of points are manually or automatically set so as to define the inside and the outside of the outline of the high-luminance region within one difference image. Subsequently, for example, the area ratio calculator 26d extracts points within another difference image that correspond to the plurality of points that have been set, based on a degree of local similarity between the images. After that, the area ratio calculator 26d calculates an area ratio corresponding to an EF by calculating areas of regions defined by the plurality of points that have been extracted from the difference images.

Figure 14:
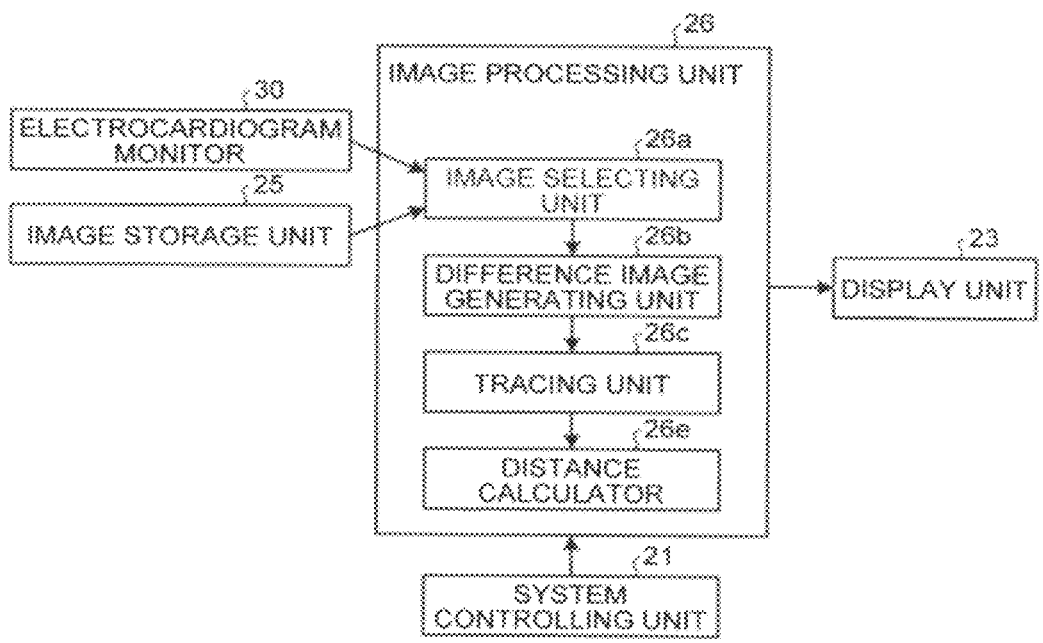
FIG. 14 is a drawing for explaining a configuration of an X-ray diagnostic apparatus according to a fourth embodiment.
Figure 16A:
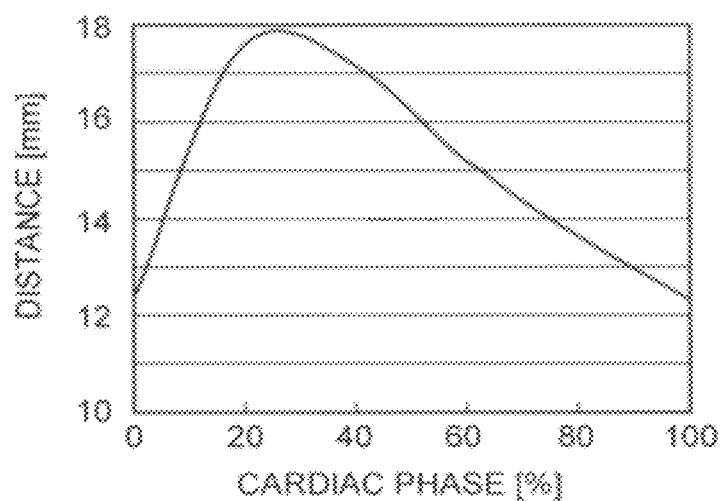
Figure 16B:
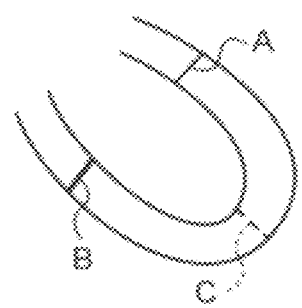
Figure 16C:
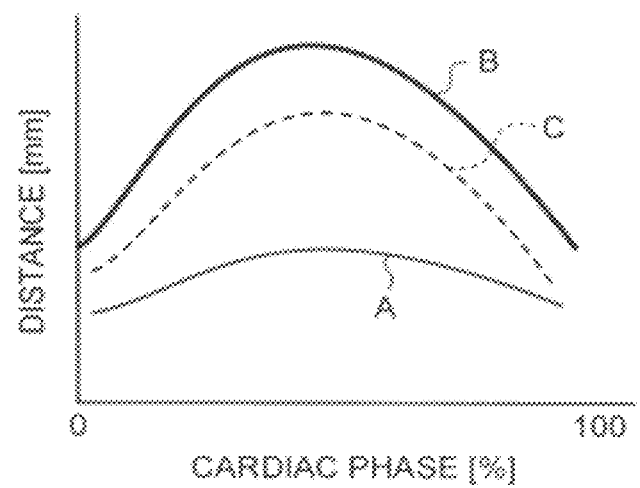

As a fourth embodiment of the present invention, an example in which an index value that is different from the one according to the third embodiment is calculated by using the difference images will be explained, with reference to FIGS. 14 to 16. FIG. 14 is a drawing for explaining a configuration of an X-ray diagnostic apparatus according to the fourth embodiment. FIGS. 15, 16A, 16B, and 16C are drawings for explaining a distance calculator.

To begin the explanation, as shown in FIG. 14, the image processing unit 26 according to the fourth embodiment is different from the image processing unit 26 according to the second embodiment explained with reference to FIG. 7 in that a distance calculator 26e is further included therein. In the following sections, the fourth embodiment will be explained while a focus is placed on this constituent element. The processes performed by the image selecting unit 26a and the difference image generating unit 26b shown in FIG. 14 are the same as the processes explained in the description of the first embodiment, whereas the process performed by the tracing unit 26c shown in FIG. 14 is the same as the process explained in the description of the second embodiment. Thus, the explanation thereof will be omitted. In addition, the image processing unit 26 according to the fourth embodiment may include the area ratio calculator 26d explained in the description of the third embodiment.

The distance calculator 26e calculates an index value (i.e., a distance) corresponding to a thickness of the myocardial tissue, by using results of the process performed by the tracing unit 26c on difference images. More specifically, the distance calculator 26e calculates, as the index value corresponding to the thickness of the myocardial tissue, a distance between a curve on the inside of an outline of a high-luminance region rendered in a difference image and a curve on the outside of the outline of the high-luminance region.

More specifically, as shown in FIG. 15, the distance calculator 26e calculates the distance between the curves on the inside and the outside of the high-luminance region in each member of the group of difference images that correspond to one heart beat and are obtained after that tracing unit 26c has performed the tracing process. After that, as shown in FIG. 16A, the distance calculator 26e generates a chart by plotting the distances that have respectively been calculated from the members of the group of difference images corresponding to the one heart beat, in correspondence with cardiac phases expressed by using an average R-R interval of the subject P as 100%.

Subsequently, the system controlling unit 21 exercises control so that the display unit 23 displays a chart as shown in, for example, FIG. 16A, as a calculation result of the distance calculator 26e.

Another arrangement is acceptable in which the distance calculator 26e performs the distance calculating process in a plurality of places within a high-luminance region. For example, as shown in FIG. 16B, the distance calculator 26e may calculate the differences at a place "A" corresponding to the anterior wall of the heart, at a place "B" corresponding to the posterior wall of the heart, and at a place "C" corresponding to the cardiac apex. After that, as shown in FIG. 16C, the distance calculator 26e generates a chart obtained by plotting the distances at the three places "A", "B", and "C" that have been calculated from each member of the group of difference images corresponding to one heart beat, in correspondence with cardiac phases expressed by using the average R-R interval of the subject P as 100%. Subsequently, the system controlling unit 21 exercises control so that the display unit 23 displays a chart as shown in FIG. 16C, as a calculation result of the distance calculator 26e. In such a chart, in the case where a large amplitude is observed in each of all the plotted results for "A", "B", and "C", medical doctors are able to confirm that the heart has a normal pulsation. On the contrary, in the chart shown in FIG. 16C, because the amplitude for "A" is small, medical doctors are able to diagnose that the movement capability of the anterior wall of the heart is degraded.

Next, a process performed by the X-ray diagnostic apparatus according to the fourth embodiment will be explained, with reference to FIG. 17. FIG. 17 is a flowchart for explaining the process performed by the X-ray diagnostic apparatus according to the fourth embodiment. With reference to FIG. 17, a process that is performed after the tracing unit 26c has generated the curve obtained by tracing the outline of the high-luminance region with respect to each member of the group of difference images corresponding to one heart beat will be explained.

As shown in FIG. 17, the X-ray diagnostic apparatus according to the fourth embodiment judges whether results of the tracing process have been output with respect to the group of difference images corresponding to one heart beat (step S401). In this situation, in the case where the tracing results have not been output (step S401: No), the X-ray diagnostic apparatus is in a stand-by state. On the contrary, in the case where the tracing results have been output (step S401: Yes), the distance calculator 26e calculates a distance corresponding to thickness of the myocardial tissue from each of the group of difference images corresponding to one heart beat by using the tracing results (step S402). In other words, the distance calculator 26e calculates, as an index value corresponding to the thickness of the myocardial tissue, the distance between a curve on the inside of an outline of a high-luminance region and a curve on the outside of the outline of the high-luminance region that is rendered in each of the difference images. Subsequently, the distance calculator 26e generates a graph by plotting the distances that have respectively been calculated from the members of the group of difference images corresponding to the one heart beat, in correspondence with cardiac phases expressed by using the average R-R interval of the subject P as 100%.

Subsequently, the system controlling unit 21 exercises control so that the display unit 23 displays a calculation result of the distance calculator 26e (e.g., a chart shown in FIG. 16A or 16C) (step S403), and the process is ended.

As explained above, according to the fourth embodiment, the distance calculator 26e performs the distance calculating process by using the curves that have respectively been generated by the tracing unit 26c with respect to the members of the group of difference images corresponding to the one heart beat. In other words, by using the result of the tracing process performed on each member of the group of difference images corresponding to the one heart beat, the distance calculator 26e calculates the distance between the curve on the inside of the outline of the high-luminance region and the curve on the outside of the outline of the high-luminance region in each the difference images, as the index value corresponding to the thickness of the myocardial tissue. With this arrangement according to the fourth embodiment, it is possible to provide medical doctors with the values with which it is possible to objectively evaluate the thickness of the myocardial tissue for each of the cardiac phases by performing only the coronary angiography process.

The distance calculator 26e may perform the process of calculating the distances by using the results of the tracing process performed by the tracing unit 26c, as explained above, or may perform the process of calculating the distances by using results of a tracing process performed by the operator on the outline of the high-luminance region in the difference images.

In the description above, the example has been explained in which the distance calculating process is performed by using the results obtained by tracing the high-luminance region. According to the fourth embodiment, however, the distance calculating process may be performed by using a method by which a plurality of points are tracked, as explained below. According to this method, for example, two points that oppose each other on the inside and the outside of a high-luminance region in one difference image are manually or automatically set. Subsequently, for example, the distance calculator 26e extracts points within another difference image that correspond to the two points that have been set, based on a degree of local similarity between the images. After that, the distance calculator 26e calculates the distances between the two points that have been extracted from the difference images as the values indicating the thickness of the myocardial tissue.

Figure 18:
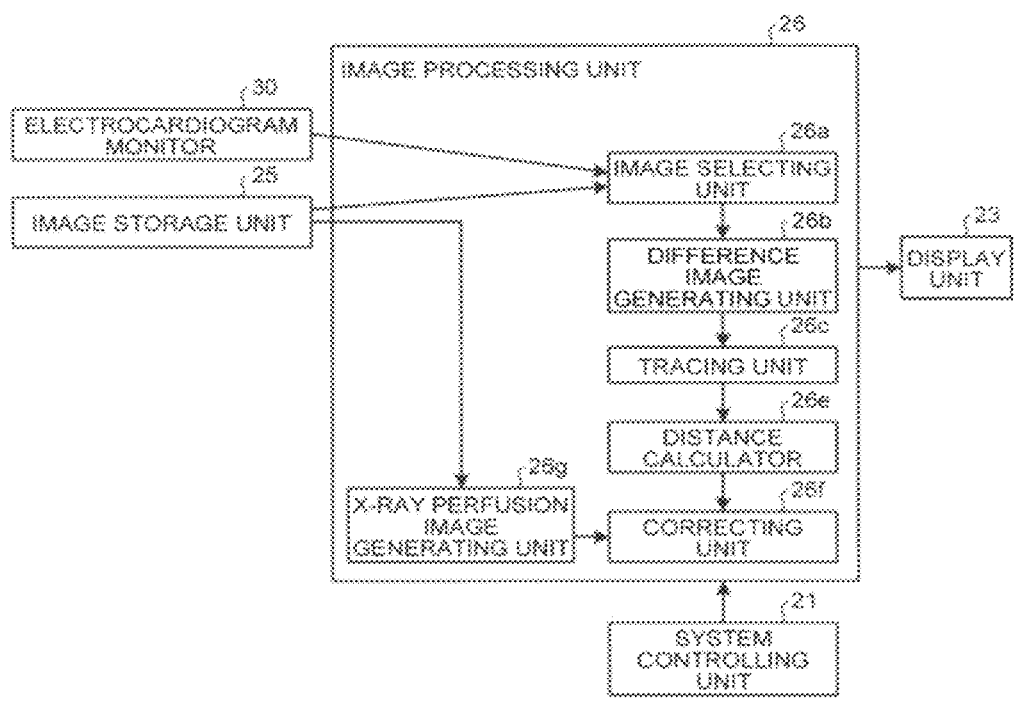
FIG. 18 is a drawing for explaining a configuration of an X-ray diagnostic apparatus according to a fifth embodiment.
Figure 19:
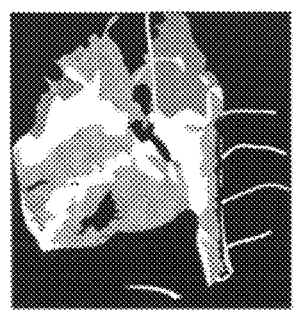
FIG. 19 is a drawing for explaining an X-ray perfusion image generating unit.
Figure 20:
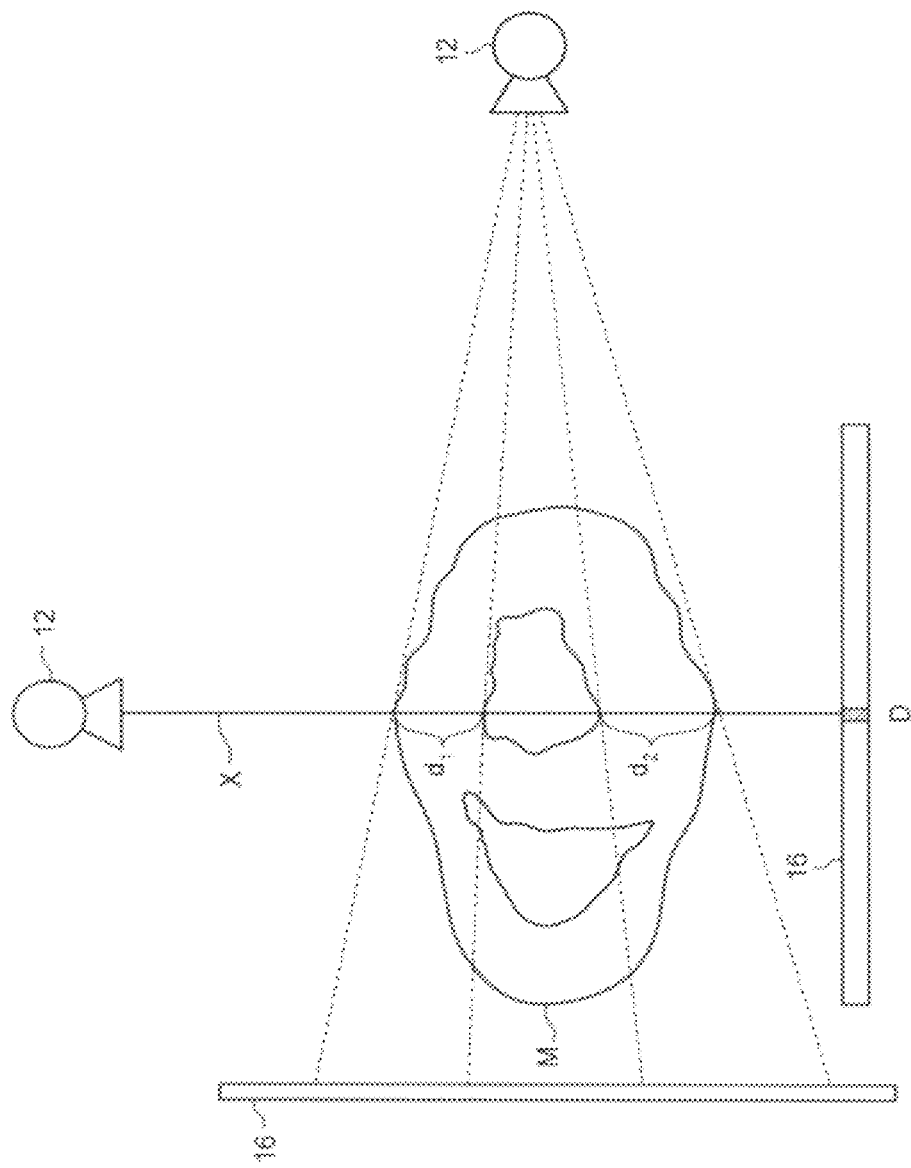
FIG. 20 is a drawing for explaining a correcting unit.

As a fifth embodiment of the present invention, an example in which an X-ray perfusion image is corrected by using the distance that indicates the thickness of the myocardial tissue and is described in the fourth embodiment will be explained with reference to FIGS. 18 to 20. FIG. 18 is a drawing for explaining a configuration of an X-ray diagnostic apparatus according to the fifth embodiment. FIG. 19 is a drawing for explaining an X-ray perfusion image generating unit. FIG. 20 is a drawing for explaining a correcting unit.

To begin the explanation, as shown in FIG. 18, the image processing unit 26 according to the fifth embodiment is different from the image processing unit 26 according to the fourth embodiment explained with reference to FIG. 14 in that a correcting unit 26f and an X-ray perfusion image generating unit 26g are further included therein. In the following sections, the fifth embodiment will be explained while a focus is placed on these constituent elements. The processes performed by the image selecting unit 26a and the difference image generating unit 26b shown in FIG. 18 are the same as the processes explained in the description of the first embodiment, whereas the process performed by the tracing unit 26c shown in FIG. 18 is the same as the process explained in the description of the second embodiment. Also, the process performed by the distance calculator 26e shown in FIG. 18 is the same as the process explained in the description of the fourth embodiment. Thus, the explanation thereof will be omitted.

For example, the X-ray perfusion image generating unit 26g generates an X-ray perfusion image indicating hemodynamics of the heart of the subject P from a plurality of X-ray transmission images that have been taken in a time sequence by radiating X-ray beams onto the heart of the subject P into which an iodine-based contrast agent has been administered. More specifically, according to the fifth embodiment, the X-ray tube radiates the X-ray beams onto the heart of the subject P into which the iodine-based contrast agent has been injected. The X-ray detecting elements included in the X-ray detector 16 transmit, to the image generating unit 24, an electrical signal converted from the X-ray beams that have passed through the subject P. With this arrangement, the image generating unit 24 generates the plurality of X-ray transmission images in the time sequence and stores the plurality of X-ray transmission images that have been generated into the image storage unit 25.

Further, the X-ray perfusion image generating unit 26g calculates an index value indicating hemodynamics by generating a time-density curve related to the index value indicating hemodynamics with respect to the pixels in each of the plurality of X-ray transmission images that have been read from the image storage unit 25 and analyzing the generated time-density curve. Subsequently, the X-ray perfusion image generating unit 26g generates the X-ray perfusion image by setting a pixel value according to the index value of each of the pixels.

In this situation, examples of the index value used for generating the X-ray perfusion image include a maximum value or a minimum value of the density of the contrast agent and a value corresponding to 90% of the maximum value of the density of the contrast agent. Other examples of the index value include a gradient of the time-density curve and an elapsed time period until the density reaches a predetermined level. Further examples of the index value include a Mean Transit Time (MTT) of the blood, a Blood Flow (BF) value, a Blood Volume (BV) value, and a value indicating the manner in which the blood flows into or out of a predetermined region. As explained here, there are a plurality of types of index values indicating hemodynamics. Thus, the X-ray perfusion image generating unit 26g can generate X-ray perfusion images of totally different types, depending on the index values being used. For example, the X-ray perfusion image generating unit 26g generates an X-ray perfusion image based on BF values, as shown in FIG. 19.

The X-ray transmission images that are taken by the X-ray diagnostic apparatus are obtained by detecting photons that have passed through the subject P by using the X-ray detector 16. For this reason, when an image of the heart has been taken, an integrated value of absorbed amounts of the photons that have passed through the myocardial tissue is expressed in the image. Thus, the X-ray perfusion image that has been generated from the X-ray transmission image includes a component related to the thickness of the myocardial tissue in the radiation direction of the X-ray beams.

More specifically, the value of each of the pixels within an X-ray perfusion image corresponding to a portion where the myocardial tissue is thick along the radiation direction is large. On the contrary, the value of each of the pixels within the X-ray perfusion image corresponding to a portion where the myocardial tissue is thin along the radiation direction is small. Accordingly, to examine the heart of the subject P by using an X-ray perfusion image, it is necessary to take the component related to the thickness of the myocardial tissue into consideration.

For these reasons, the correcting unit 26f corrects the X-ray perfusion image that has been generated by the X-ray perfusion image generating unit 26g, based on the distance corresponding to the thickness of the myocardial tissue that has been calculated by the distance calculator 26e. More specifically, when performing a coronary angiography process, the X-ray diagnostic apparatus according to the fifth embodiment radiates X-ray beams from the X-ray tube 12 toward the X-ray detector 16 onto a cross-sectional plane orthogonal to the X-ray radiation direction that is used when the X-ray transmission image used for generating the X-ray perfusion image is taken (see the dotted lines in FIG. 20). Further, the correcting unit 26f performs a correcting process by using the distances that have been calculated by the distance calculator 26e, based on a difference image that has been generated from the first X-ray transmission image.

For example, let us assume that, as shown in FIG. 20, among the paths of the X-ray beams passing through a myocardial tissue M is a path X extending from the X-ray tube 12 to reach a detecting element D included in the X-ray detector 16. Also, let an integrated amount of photons that have been detected by the detecting element D be F.

In this situation, the correcting unit 26f obtains the thickness of each of the portions of the myocardial tissue M through which the path X passes, based on information of the distances that have been calculated by the distance calculator 26e. As a result, for example, the correcting unit 26f obtains information indicating that, as shown in FIG. 20, on the path X, the thickness of the portion through which the path X passes on the X-ray tube 12 side is equal to $d_1$, whereas the thickness of the portion through which the path X passes on the X-ray detector 16 side is equal to $d_2$.

In this situation, the correcting unit 26f generates an X-ray perfusion image in which the thickness components of the myocardial tissue are corrected by, for example, multiplying the pixel value of the pixel corresponding to the detecting element D by $F/(d_1+d_2)$.

Subsequently, the system controlling unit 21 exercises control so that the display unit 23 displays the X-ray perfusion image that has been corrected by the correcting unit 26f.

In the description above, the example in which the X-ray perfusion image generating unit 26g is incorporated in the image processing unit 26 has been explained. According to the fifth embodiment, however, the process to generate the X-ray perfusion image may be performed by the image generating unit 24.

Next, a process performed by the X-ray diagnostic apparatus according to the fifth embodiment will be explained, with reference to FIG. 21. FIG. 21 is a flowchart for explaining the process performed by the X-ray diagnostic apparatus according to the fifth embodiment. Explained with reference to FIG. 21 is a process that is performed after the distance calculator 26e has performed the distance calculating process on a difference image that has been generated by radiating X-ray beams onto a cross-sectional plane orthogonal to the X-ray radiation direction that is used when the X-ray transmission image used for generating the X-ray perfusion image is taken during a coronary angiography process.

As shown in FIG. 21, the X-ray diagnostic apparatus according to the fifth embodiment judges whether an X-ray perfusion image has been generated by the X-ray perfusion image generating unit 26g (step S501). In this situation, in the case where no X-ray perfusion image has been generated (step S501: No), the X-ray diagnostic apparatus is in a standby state. On the contrary, in the case where an X-ray perfusion image has been generated (step S501: Yes), the correcting unit 26f obtains a distance (i.e., the thickness of the myocardial tissue) that has been calculated by the distance calculator 26e based on a difference image corresponding to an X-ray radiation direction with respect to a cross-sectional plane orthogonal to the X-ray radiation direction used for generating the X-ray perfusion image (step S502).

Subsequently, the correcting unit 26f corrects the X-ray perfusion image based on the obtained distance (step S503). The system controlling unit 21 exercises control so that the display unit 23 displays the X-ray perfusion image that has been corrected by the correcting unit 26f (step S504), and the process is ended.

As explained above, according to the fifth embodiment, the correcting unit 26f corrects the X-ray perfusion image that has been generated by the X-ray perfusion image generating unit 26g, based on the distance corresponding to the thickness of the myocardial tissue that has been calculated by the distance calculator 26e. With this arrangement according to the fifth embodiment, it is possible to correct the X-ray perfusion image while taking the thickness of the myocardial tissue, which is different for each examined subject, into consideration. Thus, medical doctors are able to make a diagnosis regarding cardiac functions while using the X-ray perfusion image, with a high level of precision.

In the descriptions of the first to the fifth embodiments above, the examples in which the image processing unit 26 is incorporated in each of the X-ray diagnostic apparatuses have been explained. The image processing procedures explained in the descriptions of the first to the fifth embodiments above, however, may be performed by an image processing apparatus having the same functions as those of the image processing unit 26.

As explained above, according to the first through the fifth embodiments, it is possible to generate the X-ray transmission image with which it is possible to analyze the movement functions of the heart, while reducing a burden on the subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus,. comprising:
    a difference image generating unit that generates a difference image by calculating a difference in a second X-ray transmission image from a first X-ray transmission image, the second X-ray transmission image being an image in which a myocardial tissue of an examined subject is not opacified and the first X-ray transmission image being an image in which the myocardial tissue of the examined subject is opacified with a contrast agent that has been injected into a coronary artery to opacify vessels; and
    a display controlling unit that exercises control so that a predetermined display unit displays the difference image that has been generated by the difference image generating unit.

2. The image processing apparatus according to claim 1, wherein
    the difference image generating unit generates a plurality of difference images respectively from a plurality of first X-ray transmission images, and
    the display controlling unit exercises control so that the predetermined display unit displays the plurality of difference images that have been generated by the difference image generating unit, as moving pictures or side by side.

3. The image processing apparatus according to claim 1, further comprising:
    an image selecting unit that selects the first X-ray transmission image, based on images rendered by reducing a vessel component in each of a plurality of X-ray transmission images that have been taken in a time sequence by radiating X-ray beams onto a heart of the examined subject into which the contrast agent is administered, wherein the difference image generating unit generates the difference image from the first X-ray transmission image that has been selected by the image selecting unit.

4. The image processing apparatus according to claim 1, further comprising:
an image selecting unit that selects the first X-ray transmission image out of a plurality of X-ray transmission images that have been taken in a time sequence by radiating X-ray beams onto a heart of the examined subject into which the contrast agent has been administered, based on an elapsed time period since a time at which the contrast agent is administered, or a low-frequency component within the images, or an average luminance value of an entirety of each of the images, or an average luminance value of a region of interest that has been set in each of the images, wherein
the difference image generating unit generates the difference image from the first X-ray transmission image that has been selected by the image selecting unit.

5. The image processing apparatus according to claim 1, further comprising:
an image selecting unit that selects a first X-ray transmission image derived from a left coronary angiography process and a first X-ray transmission image derived from a right coronary angiography process as the first X-ray transmission images, by selecting an X-ray transmission image in which a myocardial tissue nourished by a left coronary artery is opacified out of a plurality of X-ray transmission images that have been taken by performing the left coronary angiography process and selecting an X-ray transmission image in which a myocardial tissue nourished by a right coronary artery is opacified out of a plurality of X-ray transmission images that have been taken by performing the right coronary angiography process, wherein
the difference image generating unit generates the difference image by calculating differences in the second X-ray transmission image from the first X-ray transmission image derived from the left coronary angiography process and from the first X-ray transmission image derived from the right coronary angiography process so as to generate a difference image derived from the left coronary angiography process and a difference image derived from the right coronary angiography process and further combining together the two difference images that have been generated.

6. The image processing apparatus according to claim 3, wherein
the image selecting unit selects a plurality of first X-ray transmission images corresponding to at least one heart beat of the heart of the examined subject,
the difference image generating unit generates a plurality of difference images from the plurality of first X-ray transmission images corresponding to said at least one heart beat that have been selected by the image selecting unit, and
the display controlling unit exercises control so that the predetermined display unit displays the plurality of difference images that have been generated by the difference image generating unit, as moving pictures or side by side.

7. The image processing apparatus according to claim 4, wherein
the image selecting unit selects a plurality of first X-ray transmission images corresponding to at least one heart beat of the heart of the examined subject,
the difference image generating unit generates a plurality of difference images from the plurality of first X-ray transmission images corresponding to said at least one heart beat that have been selected by the image selecting unit, and
the display controlling unit exercises control so that the predetermined display unit displays the plurality of difference images that have been generated by the difference image generating unit, as moving pictures or side by side.

8. The image processing apparatus according to claim 5, wherein
the image selecting unit selects a plurality of first X-ray transmission images corresponding to at least one heart beat of the heart of the examined subject,
the difference image generating unit generates a plurality of difference images from the plurality of first X-ray transmission images corresponding to said at least one heart beat that have been selected by the image selecting unit, and
the display controlling unit exercises control so that the predetermined display unit displays the plurality of difference images that have been generated by the difference image generating unit, as moving pictures or side by side.

9. The image processing apparatus according to claim 1, wherein the display controlling unit exercises control so that the predetermined display unit further displays a curve obtained by tracing an outline of a high-luminance region rendered in the difference image.

10. The image processing apparatus according to claim 9, further comprising:
a tracing unit that generates a curve obtained by tracing the outline of the high-luminance region rendered in the difference image, based on pixel values of pixels included in the difference image that has been generated by the difference image generating unit, wherein
the display controlling unit exercises control so that the predetermined display unit further displays the curve that has been generated by the tracing unit.

11. The image processing apparatus according to claim 10, wherein the tracing unit generates the curve by combining an image in which vessels are opacified with the difference image.

12. The image processing apparatus according to claim 10, further comprising:
an image selecting unit that selects a first X-ray transmission image derived from a left coronary angiography process and a first X-ray transmission image derived from a right coronary angiography process as the first X-ray transmission images, by selecting an X-ray transmission image in which a myocardial tissue nourished by a left coronary artery is opacified out of a plurality of X-ray transmission images that have been taken by performing the left coronary angiography process and selecting an X-ray transmission image in which a myocardial tissue nourished by a right coronary artery is opacified out of a plurality of X-ray transmission images that have been taken by performing the right coronary angiography process, wherein
the difference image generating unit generates the difference image by calculating differences in the second X-ray transmission image from the first X-ray transmission image derived from the left coronary angiography process and from the first X-ray transmission image derived from the right coronary angiography process so as to generate a difference image derived from the left coronary angiography process and a difference image derived from the right coronary angiography process and further combining together the two difference images that have been generated, and the tracing unit generates the curve from the difference image that has been generated by combining the difference image derived from the left coronary angiography process with the difference image derived from the right coronary angiography process or the tracing unit generates the curve by generating a curve obtained tracing an outline of a high-luminous region rendered in the difference image derived from the left coronary angiography process and a curve obtained by tracing an outline of a high-luminous region rendered in the difference image derived from the right coronary angiography process and further combining together the two curves that have been generated.

13. The image processing apparatus according to claim 1, wherein the difference image generating unit generates a difference image during a systolic phase and a difference image during a diastolic phase from a first X-ray transmission image during the systolic phase and a first X-ray transmission image during the diastolic phase, respectively, and the image processing apparatus further comprises:

an area ratio calculator that calculates an area ratio between an area of a region defined by a curve obtained by tracing an inside of an outline of a high-luminance region rendered in the difference image during the systolic phase and an area of a region defined by a curve obtained by tracing an inside of an outline of a high-luminance region rendered in the difference image during the diastolic phase.

14. The image processing apparatus according to claim 13, wherein the area ratio calculator further calculates an area ratio between an area of a region defined by a curve obtained by tracing an outside of the outline of the high-luminance region rendered in the difference image during the systolic phase and an area of a region defined by a curve obtained by tracing an outside of the outline of the high-luminance region rendered in the difference image during the diastolic phase.

15. The image processing apparatus according to claim 1, further comprising:

an area calculator that calculates an area of a region defined by an outline of a high-luminance region rendered in the difference image that has been generated by the difference image generating unit.

16. The image processing apparatus according to claim 13, further comprising:

a tracing unit that generates a curve obtained by tracing an outline of a high-luminance region rendered in the difference image, based on pixel values of pixels included in the difference image that has been generated by the difference image generating unit, wherein the area ratio calculator performs an area ratio calculating process by using the curve that has been generated by the tracing unit.

17. The image processing apparatus according to claim 1, further comprising:

a distance calculator that calculates a distance between a curve on an inside of an outline of a high-luminance region rendered in the difference image that has been generated by the difference image generating unit and a curve on an outside of the outline of the high-luminance region.

18. The image processing apparatus according to claim 17, further comprising:

a tracing unit that generates a curve obtained by tracing the outline of the high-luminance region rendered in the difference image, based on pixel values of pixels included in the difference image that has been generated by the difference image generating unit, wherein the distance calculator performs a distance calculating process by using the curve that has been generated by the tracing unit.

19. The image processing apparatus according to claim 17, further comprising:

a correcting unit that corrects, based on the distance that has been calculated by the distance calculator, an X-ray perfusion image indicating hemodynamics of the heart of the examined subject and having been generated from a plurality of X-ray transmission images that have been taken in a time sequence by radiating X-ray beams onto a heart of the examined subject into which a contrast agent has been injected.

20. An image processing method,. comprising:

a process performed by a difference image generating unit to generate a difference image by calculating a difference in a second X-ray transmission image from a first X-ray transmission image, the second X-ray transmission image being an image in which a myocardial tissue of an examined subject is not opacified and the first X-ray transmission image being an image in which the myocardial tissue of the examined subject is opacified with a contrast agent that has been injected into a coronary artery to opacify vessels; and a process performed by a display controlling unit to exercise control so that a predetermined display unit displays the difference image that has been generated by the difference image generating unit.

\* \* \* \* \*